United States Patent
Tani et al.

(10) Patent No.: US 6,262,293 B1
(45) Date of Patent: Jul. 17, 2001

(54) ω-CYCLOALKLY-PROSTAGLANDIN E₂ DERIVATIVES

(75) Inventors: Kousuke Tani; Shuichi Ohuchida, both of Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/582,348

(22) PCT Filed: Dec. 24, 1998

(86) PCT No.: PCT/JP98/05863

§ 371 Date: Jun. 23, 2000

§ 102(e) Date: Jun. 23, 2000

(87) PCT Pub. No.: WO99/33794

PCT Pub. Date: Jul. 8, 1999

(30) Foreign Application Priority Data

Dec. 25, 1997 (JP) .................................................. 9-366244

(51) Int. Cl.⁷ .................................................. C07C 105/00
(52) U.S. Cl. .................................. 560/18; 560/53; 560/65; 560/66; 562/432; 562/463; 562/473; 562/474
(58) Field of Search .................................. 560/18, 53, 65, 560/66; 502/432, 463, 473, 474

(56) References Cited

U.S. PATENT DOCUMENTS

| 4,132,738 | 1/1979 | Kluender et al. . |
| 4,275,224 | 6/1981 | Kluender et al. . |

FOREIGN PATENT DOCUMENTS 54115351 7/1979 (JP) .

OTHER PUBLICATIONS

"Collection of Czechoslovak Chemical Communications," vol. 59, 1994, pp. 138–148, "Synthetic Analogues of Prostaglandins $F_{2\alpha}$ and $E_2$".

*Primary Examiner*—Robert Gerstl
(74) *Attorney, Agent, or Firm*—Stevens, Davis, Miller & Mosher, L.L.P.

(57) ABSTRACT

ω-Cycloalkyl-prostaglandin $E_2$ derivatives of formula (I)

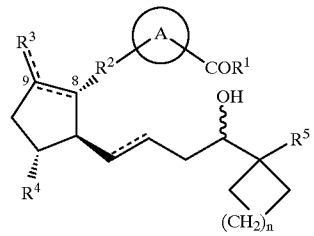

(wherein all symbols are as defined in the description); and non-toxic salts thereof, prodrugs thereof and cyclodextrin clathrates thereof.

Compounds of formula (I) strongly bind on the EP2 subtype receptor. Therefore, they are useful for prevention and/or treatment of immunological diseases (autoimmune diseases, organ transplantation etc.), asthma, abnornmal bone formation, neuronal cell death, liver damage, abortion, premature birth or retina neuropathy of glaucoma etc.

16 Claims, No Drawings

ω-CYCLOALKLY-PROSTAGLANDIN E$_2$ DERIVATIVES

TECHNICAL FIELD

This invention relates to ω-cycloalkyl-prostaglandin E$_2$ derivatives, a process for the preparation thereof, and a pharmaceutical agent containing it as an active ingredient. More particularly, this invention relates to
(1) ω-cycloalkyl-prostaglandin E$_2$ derivatives of formula

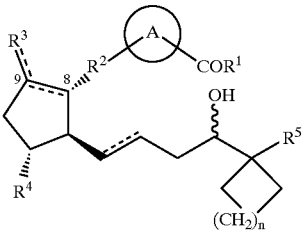

(I)

(wherein all symbols are as defined hereinafter)
or non-toxic salts thereof, or prodrugs thereof or cyclodextrin clathrates thereof,
(2) processes for the preparation thereof, and
(3) a pharmaceutical agent containing it as an active ingredient.

BACKGROUND ART

Prostaglandin E$_2$ (abbreviated as PGE$_2$ hereinafter) has been known as a metabolite in the arachidonic acid cascade. It has been known that PGE$_2$ has cyto-protective activity, uterine contractile activity, a pain-inducing effect, a promoting effect of digestive peristalsis, an awakening effect, a suppressive effect of gastric acid secretion, hypotensive activity and diuretic activity etc.

In the recent study, it was found that PGE$_2$ receptor was divided into some subtypes which possess different physiological roles each other. At present, four receptor subtypes are known and they are called EP1, EP2, EP3 and EP4 (Negishi M. et al., J. Lipid Mediators Cell Signaling, 12, 379–391 (1995)).

The present inventors investigated to find new compounds which bind on each receptor specifically, so that we found that the compounds of the present invention could bind strongly on EP2 subtype receptor and achieved the present invention.

The compounds of the present invention of formula (I), possess a strong binding activity on EP2 subtype receptor. Therefore, they are useful for prevention and/or treatment of immunological diseases (autoimmune diseases, organ transplantation etc.), asthma, abnormal bone formation, neuronal cell death, hepatopathy, abortion, premature birth or retina neuropathy of glaucoma etc.

Among the compounds of the present invention of formula (I), compounds which bind weakly on receptor subtypes except EP2 receptor and on other receptors for arachidonic acid cascade metabolites (thromboxane receptor, PGI$_2$ receptor etc.) do not express other effects and therefore, it is probable that these compounds will be medical agents which have less side-effects.

On the other hand, many patent applications of PG derivatives are known. The following application is mentioned for example.

In the specification of JP54-115351 (i.e. U.S. Pat. No. 4,275,224), a compound of formula (A)

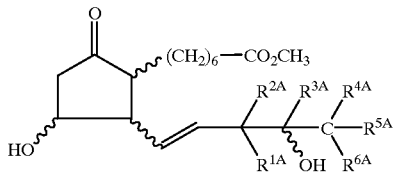

(A)

[wherein $R^{1A}$ and $R^{2A}$ are hydrogen; $R^{3A}$ is hydrogen or is taken together with $R^{4A}$ to form a methylene chain of 4 carbon atoms wherein a cycloalkyl of 6 carbon atoms inclusive is formed, or is taken together with $R^{4A}$ to form a bicycloalkenyl or bicycloalkyl moiety having the formula

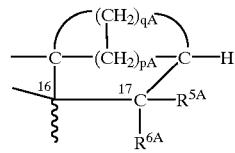

(wherein pA is an integer having a value of from 0 to 1 and qA is an integer having a value of from 2 to 3 and wherein the double bond of such bicycloalkenyl is in the qA bridge); $R^{4A}$ together with $R^{3A}$ forms a cycloalkyl, bicycloalkyl or bicycloalkenyl as defined above, or together with $R^{5A}$ forms a methylene chain of 3 carbon atoms wherein a cycloalkyl of 4 carbon atoms inclusive is formed; $R^{5A}$ is hydrogen, or is taken together with R to form a cycloalkyl as defined above; and $R^{6A}$ is hydrogen or straight-chain alkyl having 8 carbon atoms.]
are disclosed as having prostaglandin-like activity.

DISCLOSURE OF THE INVENTION

The present invention relates to
(1) an ω-cycloalkyl-prostaglandin E$_2$ derivative of formula

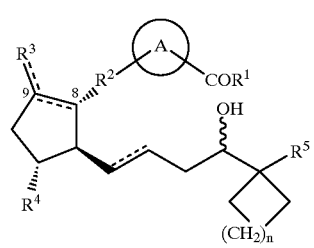

(I)

(wherein A is benzene, thiophene or furan ring;
$R^1$ is hydroxy, C1–6 alkoxy or a group of formula $NR^{10}R^{11}$ (wherein $R^{10}$ and $R^{11}$ are each independently, hydrogen atom or C1–4 alkyl);
$R^2$ is C1–4 alkylene, C2–4 alkenylene, —S—C1–4 alkylene, —S—C2–4 alkenylene or C1–4 alkylene-S—;
$R^3$ is oxo, methylene, halogen atom or a group of formula $R^{32}$—COO—

(wherein $R^{32}$ is C1–4 alkyl, C1–4 alkoxy, phenyl, phenyl-C1–4 alkyl,
$R^{33}$—OOC—C1–4 alkyl or $R^{33}$—OOC—C2–4 alkenyl
(wherein $R^{33}$ is hydrogen atom or C1–4 alkyl);

R⁴ is hydrogen atom, hydroxy or C1–4 alkoxy;
R⁵ is C1–8 alkyl, C2–8 alkenyl, C2–8 alkynyl, or C1–8 alkyl, C2–8 alkenyl or C2–8 alkynyl substituted by 1–3 substituents selected from (1)–(5) below:
(1) halogen atom,
(2) C1–4 alkoxy,
(3) C3–7 cycloalkyl,
(4) phenyl,
(5) phenyl substituted by 1–3 substituents selected from halogen atom, C1–4 alkyl, C1–4 alkoxy, nitro or trifluoromethyl;
n is 0–4;

is single bond or double bond;
with the proviso that when the C8–9 position is double bond, R³ is R³²—COO—, and R¹ is C1–6 alkoxy),
a non-toxic salt thereof, a prodrug thereof or a cyclodextrin clathrate thereof,
(2) a process for the preparation thereof, and
(3) a pharmaceutical agent containing it as an active ingredient.

In formula (I), C1–4 alkyl in the definitions of R¹¹, R¹², R³², R³³ and R⁵ means methyl, ethyl, propyl, butyl and isomers thereof.

In formula (I), C1–8 alkyl in the definitions of Rs means methyl, ethyl, propyl, butyl, pentyl, hexyl, heptyl, octyl and isomers thereof.

In formula (I), C1–4 alkoxy represented by R³², R⁴ and Rs means methoxy, ethoxy, propoxy, butoxy and isomers thereof.

In formula (I), C1–6 alkoxy represented by R' means methoxy, ethoxy, propoxy, butoxy, pentyloxy, hexyloxy and isomers thereof.

In formula (I), C2–4 alkenyl in the definitions of R³² means vinyl, propenyl, butenyl and isomers thereof.

In formula (I), C1–4 alkylene represented by R² is methylene, dimethylene, trimethylene, tetramethylene and isomers thereof.

In formula (I), C2–4 alkylene represented by R² is vinylene, propenylene, butenylene and isomers thereof.

In formula (I), C2–8 alkenyl represented by R³ means vinyl, propenyl, butenyl, pentenyl, hexenyl, heptenyl, octenyl and isomers thereof.

In formula (I), C2–8 alkynyl represented by R5 means ethynyl, propynyl, butynyl, pentynyl, hexynyl, heptynyl, octynyl and isomers thereof.

In formula (I), C3–7 cycloalkyl in the definitions of R⁵ means cyclopropyl, cyclobutyl, cyclopentyl, cyclohexyl and cycloheptyl.

In formula (I), halogen atom in the definitions of R³ and R⁵ means fluorine, chlorine, bromine and iodine.

In the present invention, it may be easily understood by those skilled in the art, unless otherwise specified, the symbol:

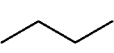

indicates that the substituent attached thereto is in front of the sheet, unless otherwise specified, the symbol:

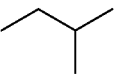

indicates that the substituent attached thereto is behind the sheet,
unless otherwise specified, the symbol:

indicates that the substituent attached thereto may be in front of or behind the sheet or may be a mixture of isomers in front of and behind the sheet.

Unless otherwise specified, all isomers are included in the present invention. For example, the alkyl, alkenyl and alkynyl groups include straight-chain and also branched-chain ones. The double bond in alkenyl group includes E, Z and EZ mixed isomers. Isomers resulting from the presence of asymmetric carbon atom(s) e.g. in branched-chain alkyl are included in the present invention.

In the present invention, in the case of a compound wherein the C7 position is sulfur, the configuration of C8 position of the compounds of the present invention are shown as 8α, but as is known in the art, these 8α-compounds are in the equilibrium state with 8β-compounds (8-epi compound). Therefore the compounds of formula (I) mean mixtures of 8α-compound and isomeric 8β-compound.

Preferred compounds of the present invention include compounds of the formula (I) listed in the examples or in Tables 1–20 below.

TABLE 1

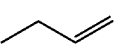

| No. | n | R⁵ |
|---|---|---|
| 1 | 0 |  |
| 2 | 0 | 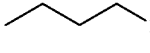 |
| 3 | 0 | 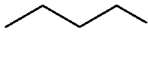 |
| 4 | 0 | 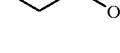 |
| 5 | 0 | 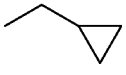 |
| 6 | 0 |  |
| 7 | 0 | 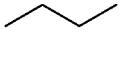 |
| 8 | 0 | |
| 9 | 0 | |
| 10 | 0 | |
| 11 | 1 | |
| 12 | 1 | |

TABLE 1-continued

[Structure: cyclopentanone with 4-carboxybenzyl-ethyl side chain, hydroxyl, and vinyl-CH(OH)-C(R⁵)(CH₂)ₙ side chain]

| No. | n | R⁵ |
|---|---|---|
| 13 | 1 | isobutyl |
| 14 | 1 | allyl (CH₂=CH-CH₂-) |
| 15 | 1 | but-3-enyl |
| 16 | 1 | pent-4-enyl |
| 17 | 1 | -(CH₂)₃-F |
| 18 | 1 | -(CH₂)₃-Cl |
| 19 | 1 | -(CH₂)₃-O-CH₃ |
| 20 | 1 | -CH₂-cyclopropyl |

TABLE 2

[Structure: cyclopentane with exocyclic =CH₂ (H₂C=), 4-carboxybenzyl-ethyl side chain, hydroxyl, and vinyl-CH(OH)-C(R⁵)(CH₂)ₙ side chain]

| No. | n | R⁵ |
|---|---|---|
| 1 | 0 | n-propyl |
| 2 | 0 | n-butyl |
| 3 | 0 | isobutyl |
| 4 | 0 | allyl |
| 5 | 0 | but-3-enyl |
| 6 | 0 | pent-4-enyl |
| 7 | 0 | -(CH₂)₃-F |
| 8 | 0 | -(CH₂)₃-Cl |
| 9 | 0 | -(CH₂)₃-O-CH₃ |
| 10 | 0 | -CH₂-cyclopropyl |
| 11 | 1 | ethyl |
| 12 | 1 | n-propyl |
| 13 | 1 | isobutyl |
| 14 | 1 | allyl |
| 15 | 1 | but-3-enyl |
| 16 | 1 | pent-4-enyl |
| 17 | 1 | -(CH₂)₃-F |
| 18 | 1 | -(CH₂)₃-Cl |
| 19 | 1 | -(CH₂)₃-O-CH₃ |
| 20 | 1 | -CH₂-cyclopropyl |

TABLE 3
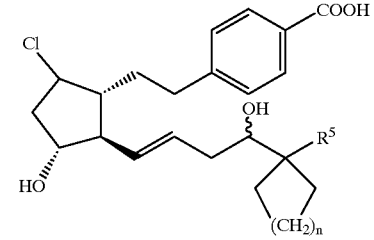
| No. | n | R⁵ |
|---|---|---|
| 1 | 0 |  |
| 2 | 0 |  |
| 3 | 0 |  |
| 4 | 0 |  |
| 5 | 0 |  |
| 6 | 0 |  |
| 7 | 0 |  |
| 8 | 0 |  |
| 9 | 0 |  |
| 10 | 0 |  |
| 11 | 1 |  |
| 12 | 1 |  |
| 13 | 1 |  |
| 14 | 1 |  |
| 15 | 1 |  |
| 16 | 1 |  |
| 17 | 1 |  |
| 18 | 1 |  |
| 19 | 1 |  |
TABLE 3-continued
| No. | n | R⁵ |
|---|---|---|
| 20 | 1 | 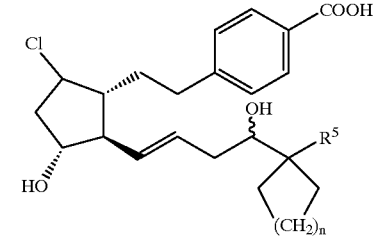 |
TABLE 4
| No. | n | R⁵ |
|---|---|---|
| 1 | 0 |  |
| 2 | 0 | 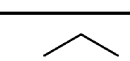 |
| 3 | 0 | 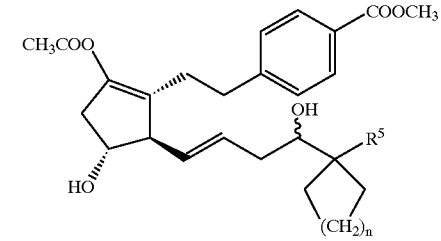 |
| 4 | 0 | 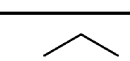 |
| 5 | 0 |  |
| 6 | 0 | 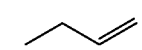 |
| 7 | 0 | 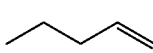 |
| 8 | 0 | 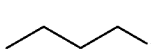 |
| 9 | 0 |  |
| 10 | 0 |  |
| 11 | 1 |  |
| 12 | 1 |  |

TABLE 4-continued

[Structure: cyclopentane with CH3COO, OH, HO, connected to chain bearing OH, R5, (CH2)n cyclic group, and phenyl-COOCH3]

| No. | n | R⁵ |
|---|---|---|
| 13 | 1 | sec-butyl (CH2CH(CH3)CH2-) |
| 14 | 1 | allyl (CH2=CHCH2-) |
| 15 | 1 | but-3-enyl |
| 16 | 1 | pent-4-enyl |
| 17 | 1 | -(CH2)4F |
| 18 | 1 | -(CH2)4Cl |
| 19 | 1 | -(CH2)4OCH3 |
| 20 | 1 | -CH2-cyclopropyl |

TABLE 5

[Structure: cyclopentanone with S-CH2-phenyl-COOH, OH, HO, connected to chain bearing OH, R5, (CH2)n cyclic group]

| No. | n | R⁵ |
|---|---|---|
| 1 | 0 | propyl |
| 2 | 0 | butyl |
| 3 | 0 | isobutyl |
| 4 | 0 | vinyl (CH2=CH-) |

TABLE 5-continued

[Structure: cyclopentanone with S-CH2-phenyl-COOH, OH, HO, connected to chain bearing OH, R5, (CH2)n cyclic group]

| No. | n | R⁵ |
|---|---|---|
| 5 | 0 | allyl |
| 6 | 0 | but-3-enyl |
| 7 | 0 | -(CH2)4F |
| 8 | 0 | -(CH2)4Cl |
| 9 | 0 | -(CH2)4OCH3 |
| 10 | 0 | -CH2-cyclopropyl |
| 11 | 1 | ethyl |
| 12 | 1 | propyl |
| 13 | 1 | isopropyl (or sec-butyl) |
| 14 | 1 | vinyl |
| 15 | 1 | allyl |
| 16 | 1 | but-3-enyl |
| 17 | 1 | -(CH2)4F |
| 18 | 1 | -(CH2)4Cl |
| 19 | 1 | -(CH2)4OCH3 |
| 20 | 1 | -CH2-cyclopropyl |

TABLE 6

[Structure: cyclopentane with =CH2, HO, and side chain with S-CH2-C6H4-COOH, vinyl, OH, R5, (CH2)n]

| No. | n | R5 |
|---|---|---|
| 1 | 0 | propyl |
| 2 | 0 | butyl |
| 3 | 0 | isobutyl |
| 4 | 0 | allyl (CH2-CH=CH2) |
| 5 | 0 | but-3-enyl |
| 6 | 0 | pent-4-enyl |
| 7 | 0 | 4-fluorobutyl |
| 8 | 0 | 4-chlorobutyl |
| 9 | 0 | 3-methoxypropyl (CH2CH2CH2OCH3) |
| 10 | 0 | cyclopropylmethyl |
| 11 | 1 | propyl |
| 12 | 1 | butyl |
| 13 | 1 | isobutyl |
| 14 | 1 | allyl |
| 15 | 1 | but-3-enyl |
| 16 | 1 | pent-4-enyl |
| 17 | 1 | 4-fluorobutyl |
| 18 | 1 | 4-chlorobutyl |
| 19 | 1 | 3-methoxypropyl |

TABLE 6-continued

| No. | n | R5 |
|---|---|---|
| 20 | 1 | cyclopropylmethyl |

TABLE 7

[Structure: cyclopentane with Cl, HO, and side chain with S-CH2-C6H4-COOH, vinyl, OH, R5, (CH2)n]

| No. | n | R5 |
|---|---|---|
| 1 | 0 | propyl |
| 2 | 0 | butyl |
| 3 | 0 | isobutyl |
| 4 | 0 | allyl |
| 5 | 0 | but-3-enyl |
| 6 | 0 | pent-4-enyl |
| 7 | 0 | 4-fluorobutyl |
| 8 | 0 | 4-chlorobutyl |
| 9 | 0 | 3-methoxypropyl |
| 10 | 0 | cyclopropylmethyl |
| 11 | 1 | propyl |
| 12 | 1 | butyl |

TABLE 7-continued
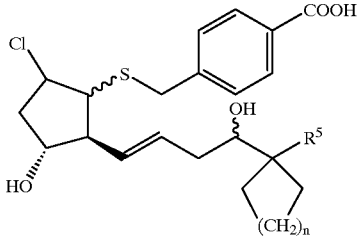
| No. | n | R⁵ |
|---|---|---|
| 13 | 1 | 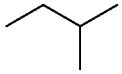 |
| 14 | 1 |  |
| 15 | 1 |  |
| 16 | 1 | 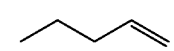 |
| 17 | 1 | 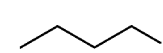 |
| 18 | 1 |  |
| 19 | 1 |  |
| 20 | 1 | 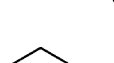 |
TABLE 8
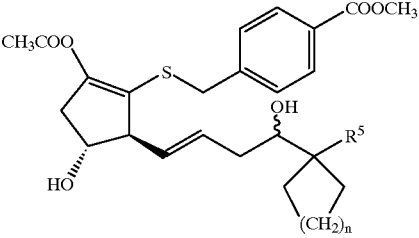
| No. | n | R⁵ |
|---|---|---|
| 1 | 0 | 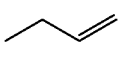 |
| 2 | 0 | 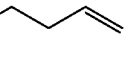 |
| 3 | 0 | 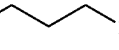 |
| 4 | 0 |  |
TABLE 8-continued
| No. | n | R⁵ |
|---|---|---|
| 5 | 0 | 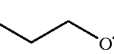 |
| 6 | 0 | 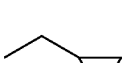 |
| 7 | 0 | 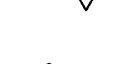 |
| 8 | 0 | 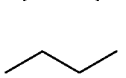 |
| 9 | 0 | 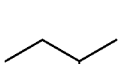 |
| 10 | 0 |  |
| 11 | 1 | 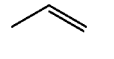 |
| 12 | 1 | 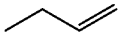 |
| 13 | 1 | 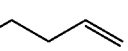 |
| 14 | 1 |  |
| 15 | 1 |  |
| 16 | 1 | 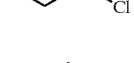 |
| 17 | 1 | 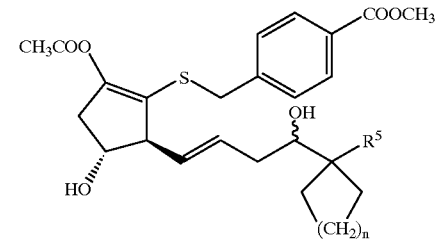 |
| 18 | 1 | 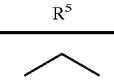 |
| 19 | 1 | 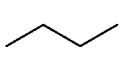 |
| 20 | 1 | 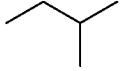 |

TABLE 9
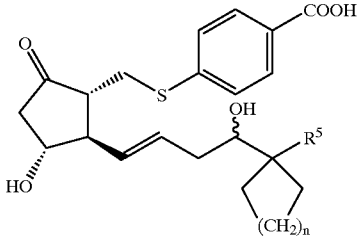
| No. | n | R⁵ |
|---|---|---|
| 1 | 0 |  |
| 2 | 0 | 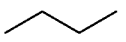 |
| 3 | 0 | 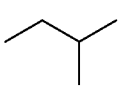 |
| 4 | 0 |  |
| 5 | 0 |  |
| 6 | 0 |  |
| 7 | 0 | 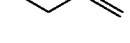 |
| 8 | 0 |  |
| 9 | 0 | 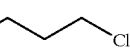 |
| 10 | 0 | 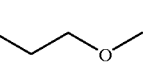 |
| 11 | 1 |  |
| 12 | 1 | 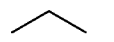 |
| 13 | 1 | 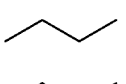 |
| 14 | 1 |  |
| 15 | 1 | 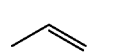 |
| 16 | 1 |  |
| 17 | 1 | 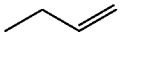 |
| 18 | 1 | 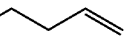 |
| 19 | 1 |  |
TABLE 9-continued
| No. | n | R⁵ |
|---|---|---|
| 20 | 1 | 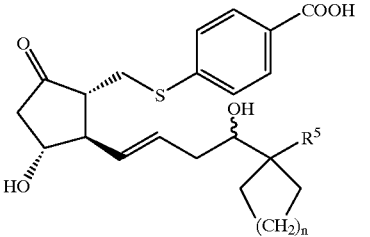 |
TABLE 10
| No. | n | R⁵ |
|---|---|---|
| 1 | 0 |  |
| 2 | 0 | 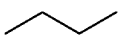 |
| 3 | 0 | 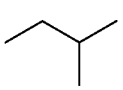 |
| 4 | 0 |  |
| 5 | 0 |  |
| 6 | 0 | 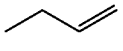 |
| 7 | 0 | 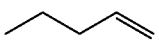 |
| 8 | 0 | 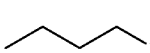 |
| 9 | 0 |  |
| 10 | 0 | |
| 11 | 1 | |
| 12 | 1 | |

TABLE 10-continued
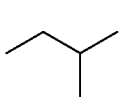
| No. | n | R⁵ |
|---|---|---|
| 13 | 1 | 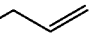 |
| 14 | 1 |  |
| 15 | 1 | 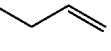 |
| 16 | 1 |  |
| 17 | 1 | 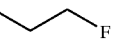 |
| 18 | 1 |  |
| 19 | 1 | 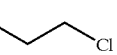 |
| 20 | 1 |  |
TABLE 11
| No. | n | R⁵ |
|---|---|---|
| 1 | 0 |  |
| 2 | 0 | 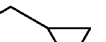 |
| 3 | 0 |  |
| 4 | 0 |  |
TABLE 11-continued
| No. | n | R⁵ |
|---|---|---|
| 5 | 0 |  |
| 6 | 0 |  |
| 7 | 0 |  |
| 8 | 0 |  |
| 9 | 0 | 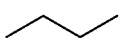 |
| 10 | 0 | 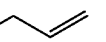 |
| 11 | 1 | 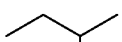 |
| 12 | 1 | 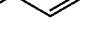 |
| 13 | 1 |  |
| 14 | 1 | 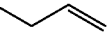 |
| 15 | 1 | 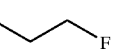 |
| 16 | 1 |  |
| 17 | 1 | |
| 18 | 1 | |
| 19 | 1 | |
| 20 | 1 |  |

TABLE 12

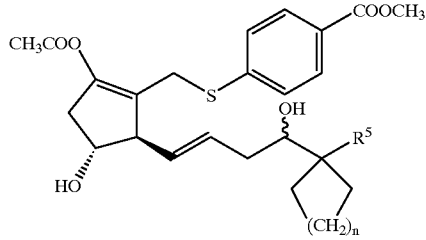

| No. | n | R⁵ |
|---|---|---|
| 1 | 0 | (isobutyl) |
| 2 | 0 | (n-butyl) |
| 3 | 0 | (isopentyl) |
| 4 | 0 | (allyl) |
| 5 | 0 | (butenyl) |
| 6 | 0 | (pentenyl) |
| 7 | 0 | (fluorobutyl) |
| 8 | 0 | (chlorobutyl) |
| 9 | 0 | (methoxybutyl) |
| 10 | 0 | (cyclopropylmethyl) |
| 11 | 1 | (isobutyl) |
| 12 | 1 | (n-butyl) |
| 13 | 1 | (isopentyl) |
| 14 | 1 | (allyl) |
| 15 | 1 | (butenyl) |
| 16 | 1 | (pentenyl) |
| 17 | 1 | (fluorobutyl) |
| 18 | 1 | (chlorobutyl) |
| 19 | 1 | (methoxybutyl) |

TABLE 12-continued

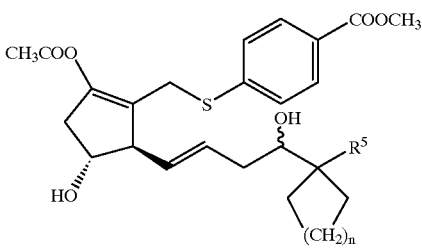

| No. | n | R⁵ |
|---|---|---|
| 20 | 1 | (cyclopropylmethyl) |

TABLE 13

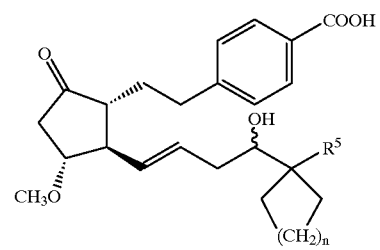

| No. | n | R⁵ |
|---|---|---|
| 1 | 0 | (isobutyl) |
| 2 | 0 | (n-butyl) |
| 3 | 0 | (isopentyl) |
| 4 | 0 | (allyl) |
| 5 | 0 | (butenyl) |
| 6 | 0 | (pentenyl) |
| 7 | 0 | (fluorobutyl) |
| 8 | 0 | (chlorobutyl) |
| 9 | 0 | (methoxybutyl) |
| 10 | 0 | (cyclopropylmethyl) |
| 11 | 1 | (isobutyl) |

TABLE 13-continued

[Structure: cyclopentanone with CH3O, connected via CH2CH2 to phenyl-COOH, and alkenyl chain with OH, cyclopentyl ring bearing $R^5$ and $(CH_2)_n$]

| No. | n | $R^5$ |
|---|---|---|
| 12 | 1 | n-butyl |
| 13 | 1 | isobutyl |
| 14 | 1 | vinyl |
| 15 | 1 | allyl |
| 16 | 1 | but-3-enyl |
| 17 | 1 | (CH$_2$)$_3$F |
| 18 | 1 | (CH$_2$)$_3$Cl |
| 19 | 1 | (CH$_2$)$_3$OCH$_3$ |
| 20 | 1 | cyclopropylmethyl |

TABLE 14

[Structure: cyclopentane with exocyclic =CH$_2$, CH3O, connected via CH2CH2 to phenyl-COOH, and alkenyl chain with OH, cyclopentyl ring bearing $R^5$ and $(CH_2)_n$]

| No. | n | $R^5$ |
|---|---|---|
| 1 | 0 | ethyl |
| 2 | 0 | n-propyl |
| 3 | 0 | isopropyl |
| 4 | 0 | vinyl |
| 5 | 0 | allyl |
| 6 | 0 | but-3-enyl |
| 7 | 0 | (CH$_2$)$_3$F |
| 8 | 0 | (CH$_2$)$_3$Cl |
| 9 | 0 | (CH$_2$)$_3$OCH$_3$ |
| 10 | 0 | cyclopropylmethyl |
| 11 | 1 | ethyl |
| 12 | 1 | n-butyl |
| 13 | 1 | isobutyl |
| 14 | 1 | vinyl |
| 15 | 1 | allyl |
| 16 | 1 | but-3-enyl |
| 17 | 1 | (CH$_2$)$_3$F |
| 18 | 1 | (CH$_2$)$_3$Cl |
| 19 | 1 | (CH$_2$)$_3$OCH$_3$ |
| 20 | 1 | cyclopropylmethyl |

TABLE 15

[Structure: cyclopentane with Cl, OCH₃, and side chain to phenyl-COOH; OH, R⁵, (CH₂)ₙ]

| No. | n | R⁵ |
|-----|---|-----|
| 1 | 0 | ethyl |
| 2 | 0 | propyl |
| 3 | 0 | isopropyl |
| 4 | 0 | vinyl |
| 5 | 0 | allyl |
| 6 | 0 | 3-butenyl |
| 7 | 0 | (CH₂)₃F |
| 8 | 0 | (CH₂)₃Cl |
| 9 | 0 | (CH₂)₃OCH₃ |
| 10 | 0 | cyclopropylmethyl |
| 11 | 1 | ethyl |
| 12 | 1 | propyl |
| 13 | 1 | isopropyl |
| 14 | 1 | vinyl |
| 15 | 1 | allyl |
| 16 | 1 | 3-butenyl |
| 17 | 1 | (CH₂)₃F |
| 18 | 1 | (CH₂)₃Cl |
| 19 | 1 | (CH₂)₃OCH₃ |

TABLE 15-continued

| No. | n | R⁵ |
|-----|---|-----|
| 20 | 1 | cyclopropylmethyl |

TABLE 16

[Structure: cyclopentene with CH₃COO, OCH₃, and side chain to phenyl-COOCH₃; OH, R⁵, (CH₂)ₙ]

| No. | n | R⁵ |
|-----|---|-----|
| 1 | 0 | ethyl |
| 2 | 0 | propyl |
| 3 | 0 | isopropyl |
| 4 | 0 | vinyl |
| 5 | 0 | allyl |
| 6 | 0 | 3-butenyl |
| 7 | 0 | (CH₂)₃F |
| 8 | 0 | (CH₂)₃Cl |
| 9 | 0 | (CH₂)₃OCH₃ |
| 10 | 0 | cyclopropylmethyl |
| 11 | 1 | ethyl |

TABLE 16-continued

[Structure: cyclopentene with CH3COO, CH3O, OH, R5, (CH2)n substituents and COOCH3 phenyl group]

| No. | n | R⁵ |
|---|---|---|
| 12 | 1 | n-propyl |
| 13 | 1 | isobutyl |
| 14 | 1 | vinyl |
| 15 | 1 | allyl |
| 16 | 1 | but-3-enyl |
| 17 | 1 | (CH2)3F |
| 18 | 1 | (CH2)3Cl |
| 19 | 1 | (CH2)3OCH3 |
| 20 | 1 | CH2-cyclopropyl |

TABLE 17

[Structure: cyclopentanone with COOH phenyl group, OH, R5, (CH2)n substituents]

| No. | n | R⁵ |
|---|---|---|
| 1 | 0 | ethyl |
| 2 | 0 | n-propyl |
| 3 | 0 | isopropyl |
| 4 | 0 | vinyl |

TABLE 17-continued

[Structure: cyclopentanone with COOH phenyl group, OH, R5, (CH2)n substituents]

| No. | n | R⁵ |
|---|---|---|
| 5 | 0 | allyl |
| 6 | 0 | but-3-enyl |
| 7 | 0 | (CH2)3F |
| 8 | 0 | (CH2)3Cl |
| 9 | 0 | (CH2)3OCH3 |
| 10 | 0 | CH2-cyclopropyl |
| 11 | 1 | ethyl |
| 12 | 1 | n-propyl |
| 13 | 1 | isobutyl |
| 14 | 1 | vinyl |
| 15 | 1 | allyl |
| 16 | 1 | but-3-enyl |
| 17 | 1 | (CH2)3F |
| 18 | 1 | (CH2)3Cl |
| 19 | 1 | (CH2)3OCH3 |
| 20 | 1 | CH2-cyclopropyl |

TABLE 18

Structure: cyclopentane core with exocyclic =CH₂ group, substituent chain with CH₂CH₂-(p-C₆H₄-COOH), and side chain CH=CH-CH₂-CH(OH)-C(R⁵)((CH₂)ₙ ring).

| No. | n | R⁵ |
|---|---|---|
| 1 | 0 | n-propyl |
| 2 | 0 | n-butyl |
| 3 | 0 | isobutyl |
| 4 | 0 | vinyl (-CH=CH₂) |
| 5 | 0 | allyl (-CH₂-CH=CH₂) |
| 6 | 0 | 3-butenyl |
| 7 | 0 | -(CH₂)₄-F |
| 8 | 0 | -(CH₂)₄-Cl |
| 9 | 0 | -(CH₂)₃-OCH₃ |
| 10 | 0 | cyclopropylmethyl |
| 11 | 1 | n-propyl |
| 12 | 1 | n-butyl |
| 13 | 1 | isobutyl |
| 14 | 1 | allyl |
| 15 | 1 | 2-butenyl |
| 16 | 1 | 3-butenyl |
| 17 | 1 | -(CH₂)₄-F |
| 18 | 1 | -(CH₂)₄-Cl |
| 19 | 1 | -(CH₂)₃-OCH₃ |
| 20 | 1 | cyclopropylmethyl |

TABLE 19

Structure: same core but with Cl substituent (instead of =CH₂) on the cyclopentane.

| No. | n | R⁵ |
|---|---|---|
| 1 | 0 | n-propyl |
| 2 | 0 | n-butyl |
| 3 | 0 | isobutyl |
| 4 | 0 | vinyl |
| 5 | 0 | allyl |
| 6 | 0 | 3-butenyl |
| 7 | 0 | -(CH₂)₄-F |
| 8 | 0 | -(CH₂)₄-Cl |
| 9 | 0 | -(CH₂)₃-OCH₃ |
| 10 | 0 | cyclopropylmethyl |
| 11 | 1 | n-propyl |

TABLE 19-continued

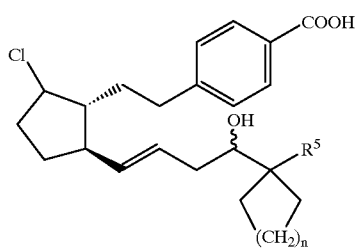

| No. | n | R⁵ |
|---|---|---|
| 12 | 1 | n-butyl |
| 13 | 1 | isobutyl |
| 14 | 1 | allyl |
| 15 | 1 | but-3-enyl |
| 16 | 1 | pent-4-enyl |
| 17 | 1 | 4-fluorobutyl |
| 18 | 1 | 4-chlorobutyl |
| 19 | 1 | 4-methoxybutyl |
| 20 | 1 | cyclopropylmethyl |

TABLE 20

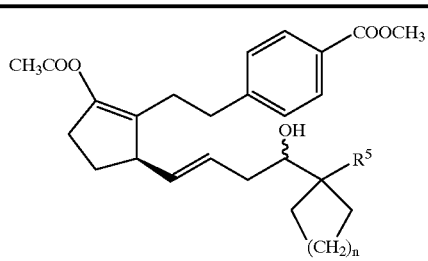

| No. | n | R⁵ |
|---|---|---|
| 1 | 0 | ethyl |
| 2 | 0 | n-propyl |
| 3 | 0 | isopropyl |
| 4 | 0 | vinyl |

TABLE 20-continued

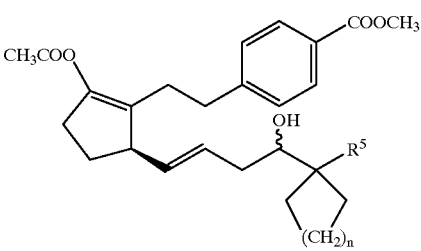

| No. | n | R⁵ |
|---|---|---|
| 5 | 0 | allyl |
| 6 | 0 | but-3-enyl |
| 7 | 0 | 3-fluoropropyl |
| 8 | 0 | 3-chloropropyl |
| 9 | 0 | 3-methoxypropyl |
| 10 | 0 | cyclopropyl |
| 11 | 1 | ethyl |
| 12 | 1 | n-propyl |
| 13 | 1 | isopropyl |
| 14 | 1 | vinyl |
| 15 | 1 | allyl |
| 16 | 1 | but-3-enyl |
| 17 | 1 | 4-fluorobutyl |
| 18 | 1 | 4-chlorobutyl |
| 19 | 1 | 4-methoxybutyl |
| 20 | 1 | cyclopropylmethyl |

[Salts]

The compounds of the present invention of formula (I) may be converted into the corresponding salts by a conventional means. Non-toxic, and water-soluble salts are preferable. Appropriate salts are described below; salts of alkali metals (potassium, sodium etc.), salts of alkaline-earth metals (calcium, magnesium etc.), ammonium salts, salts of pharmaceutically acceptable organic amines (tetramethyl ammonium, triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine etc.).

[Cyclodextrin clathrates]

Prostanic acid derivatives of formula (I) may be converted into cyclodextrin clathrates using α-, β- or γ-cyclodextrin or a mixture thereof, by the methods described in the specification of Japanese Kokoku No.50-3363 or Japanese Kokoku No.52-31404 (i.e. GB Patent Nos. 1351238 or 1419221). Converting into their cyclodextrin clathrates serves to increase the stability and solubility in water of the compounds, and therefore it is useful in the use for pharmaceuticals.

BEST MODE FOR CARRYING OUT THE INVENTION (1) Among the compounds of the present invention of formula (I), a compound (wherein $R^3$ is oxo, methylene or halogen atom; $R^1$ is hydroxy); i.e. a compound of formula (IA)

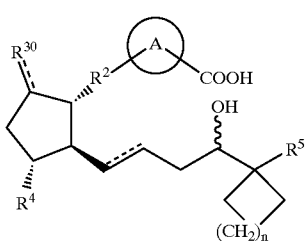

(IA)

wherein $R^{30}$ is oxo, methylene or halogen atom, and the other symbols are as defined above)
may be prepared by subjecting to hydrolysis using an enzyme or hydrolysis under alkaline conditions a compound of formula (IB)

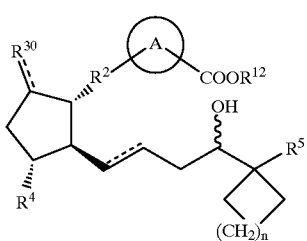

(IB)

(wherein $R^{12}$ is C1–6 alkyl, and the other symbols are as defined above).

Hydrolysis using an enzyme is known, for example, it may be carried out in a mixture of a water-miscible organic solvent (ethanol, dimethylsulfoxide etc.) and water, in the presence or absence of buffer, using an ester-cleaving enzyme (esterase, lipase etc.) at a temperature of from 0° C. to 50° C.

Hydrolysis under alkaline conditions is known, for example, it may be carried out in awater-miscible organic solvent (ethanol, tetrahydrofuran (THF), dioxane etc.) using an aqueous solution of an alkali (sodium hydroxide, potassium hydroxide, potassium carbonate etc.) at a temperature of from −10° C. to 90° C.

(2) Among the compounds of the present invention of formula (I), a compound (wherein $R^3$ is oxo, methylene or halogen atom; $R^1$ is a group of formula $NR^{10}R^{11}$ (wherein all symbols are as defined above)); i.e. a compound of formula (IC)

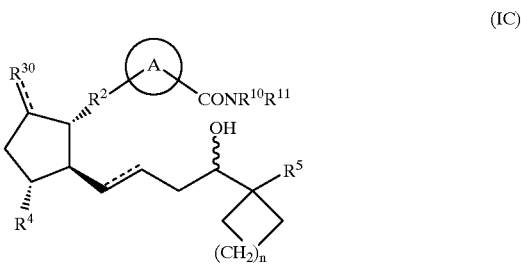

(IC)

(wherein all symbols are as defined above)
may be prepared by amidation of a compound of formula (IA)

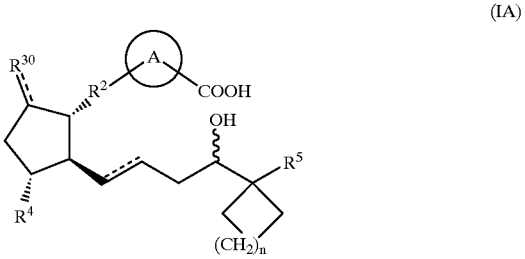

(IA)

(wherein all symbols are as defined above)
with a compound of formula (II)

$HNR^{10}R^{11}$ (II)

(wherein all symbols are as defined above).

Amidation is known, for example, it may be carried out in an inert organic solvent (THF, methylene chloride, benzene, acetone, acetonitrile or a mixture thereof etc.), in the presence or absence of a tertiary amine (dimethylaminopyridine, pyridine, triethylamine etc.), using a condensing agent (1,3-dicyclohexylcarbodiimide (DCC), 1-ethyl-3-[3-(dimethylamino) propyl]carbodiimide (EDC) etc.) at a temperature of from 0° C. to 50° C.

(3) Among the compounds of formula (IB), a compound (wherein $R^4$ is hydrogen atom or hydroxy); i.e. a compound of formula (IB-1)

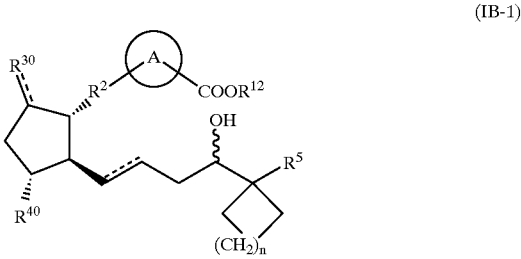

(IB-1)

(wherein $R^{40}$ is hydrogen atom or hydroxy, and the other symbols are as defined above)

may be prepared by deprotection reaction under acidic conditions of a compound of formula (III)

(III)

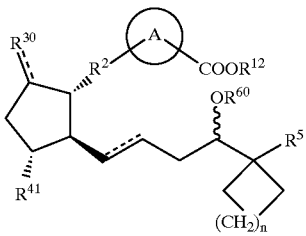

(wherein $R^{41}$ is hydrogen atom or hydroxy protected by a protective group which may be removed under acidic conditions; $R^{60}$ is a protective group of hydroxy which may be removed under acidic conditions, and the other symbols are as defined above.)

A protective group of hydroxy which may be removed under acidic conditions includes, for example, t-butyldimethylsilyl, triphenylmethyl, tetrahydropyran-2-yl etc.

Hydrolysis under acidic conditions is known; for example, it may be carried out in a water-miscible organic solvent (tetrahydrofuran, methanol, ethanol, dimethoxyethane, acetonitrile or a mixture thereof etc.) using an inorganic acid (hydrochloric acid, phosphoric acid, hydrofluoric acid, hydrofluoric acid-pyridine complex etc.) or an organic acid (acetic acid, toluenesulfonic acid, trichloroacetic acid etc.), at a temperature of from 0° C. to 50° C.

(4) Among the compounds of formula (IB), a compound (wherein $R^{40}$ is C1–4 alkoxy); i.e. a compound of formula (IB-2)

(IB-2)

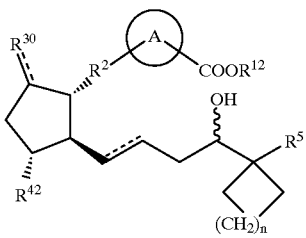

(wherein R 42 is C1–4 alkoxy and the other symbols are as defined above) may be prepared by O-alkylation of a compound of formula (IB) wherein $R^4$ is hydroxy, i.e. a compound of formula (IB-3)

(IB-3)

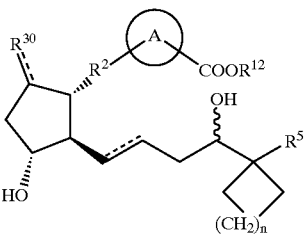

(wherein all symbols are as defined above).

O-Alkylation is known, for example, it may be carried out in an inert organic solvent (THF, diethyl ether etc.), using diazoalkane at a temperature of from −30° C. to 40° C. or in an inert organic solvent (acetonitrile etc.), in the presence of silver oxide, using alkyl iodide at a temperature of from 0° C. to 40° C.

(5) Among the compounds of formula (I) wherein $R^3$ is a group of formula

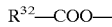

$R^{32}$—COO—

(wherein $R^{32}$ is as defined above); $R^1$ is C1–6 alkoxy); i.e. a compound of formula (ID)

(ID)

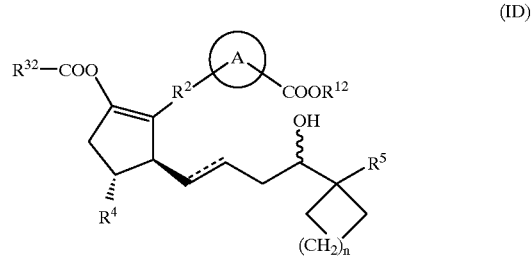

(wherein all symbols are as defined above)

may be prepared by deprotection under acidic conditions of a compound of formula (IV)

(IV)

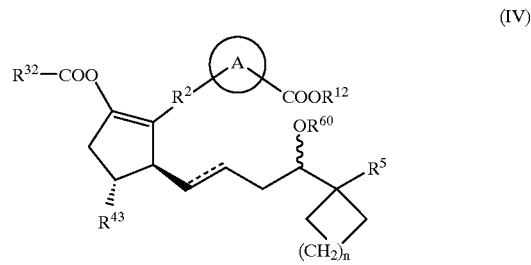

(wherein all symbols are as defined above).

Deprotection reaction may be carried out as described above.

A compound of formula (IV) may be prepared by scheme (G) or (K) described below.

A compound of formula (III) may be divided into the following six classes of compounds according to the values of $R^{30}$ and $R^{41}$. That is, 1) $R^{30}$ is oxo and $R^{41}$ is hydroxy protected by a protective group which may be removed under acidic conditions, i.e. a compound of formula (IIIA)

(IIIA)

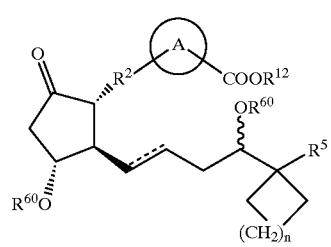

wherein all symbols are as defined above).

2) $R^{30}$ is methylene and $R^{41}$ is hydroxy protected by a protective group which may be removed under acidic conditions, i.e. a compound of formula (IIIB)

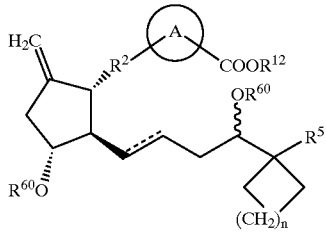

(IIIB)

(wherein all symbols are as defined above).

3) $R^{30}$ is halogen atom and $R^{41}$ is hydroxy protected by a protective group which may be removable under acidic conditions, i.e. a compound of formula (IIIC)

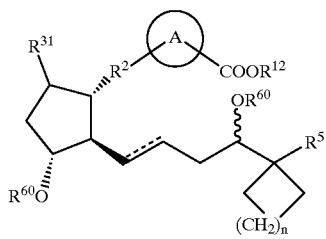

(IIIC)

(wherein $R^{31}$ is halogen atom, and the other symbols are as defined above).

4) $R^{30}$ is oxo; $R^{41}$ is hydrogen atom, i.e. a compound of formula (IIID)

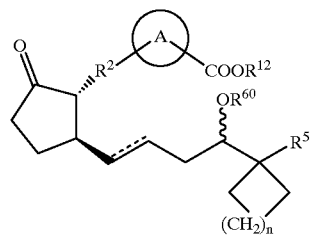

(IIID)

(wherein all symbols are as defined above).

5) $R^{30}$ is methylene and $R^{41}$ is hydrogen atom, i.e. a compound of formula (IIIE)

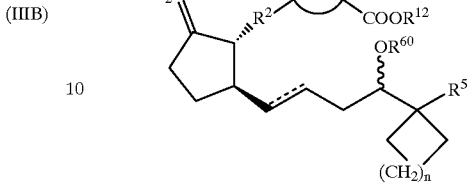

(IIIE)

(wherein all symbols are as defined above).

6) $R^{30}$ is halogen atom and $R^{41}$ is hydrogen atom, i.e. a compound of formula (IIIF)

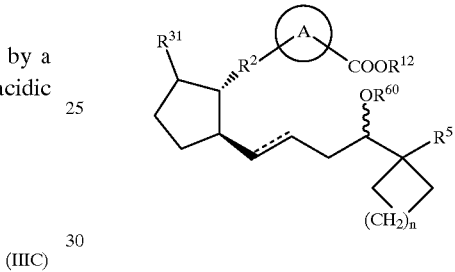

(IIIF)

(wherein all symbols are as defined above).

A compound of formula (IIIB) may be prepared from a compound of formula (IIIA) according to the reaction of the following Scheme (A).

A compound of formula (IIIC) may be prepared from a compound of formula (IIIA) according to the reactions of the following Scheme (B), (C) or (D).

A compound of formula (IIID) may be prepared from a compound of formula (IIA) according to the reactions of the following Scheme (E).

A compound of formula (IIIE) may be prepared from a compound of formula (IIID) according to the same reactions as the following Scheme (A).

A compound of formula (IIIF) may be prepared from a compound of formula (IIID) according to the same reactions as the following Scheme (B), (C) or (D).

A compound of formula (IIIA) may be prepared according to the reactions of the following Scheme (F), (G), (H) or (J).

In the reaction Schemes, the symbols represent the following meanings or are as described above.

$R^{21}$ is C1–3 alkylene or C2–3 alkenylene;
$R^{22}$ is C1–3 alkylene;
t-Bu is t-butyl;
n-Bu is normal butyl;
c-Hex is cyclohexyl;
Et is ethyl;
EE is ethoxyethyl;
Ac is acetyl;
Ph is phenyl;
Ts is p-toluenesulfonyl;
Ms is methanesulfonyl;
DMAP is dimethylaminopyridine;
AIBN is 2,2'-azobisisobutyronitrile;
DIBAL is diisobutylaluminum hydride;

Scheme (A)
-continued
Scheme (B)
Scheme (C)

-continued
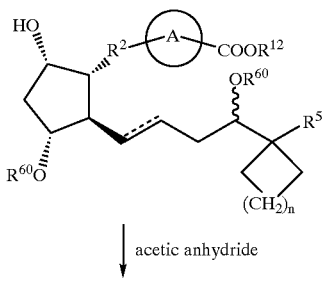
↓ acetic anhydride
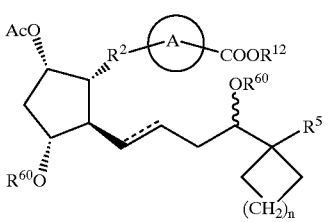
↓ Deprotection
↓ Separation of 16αβ
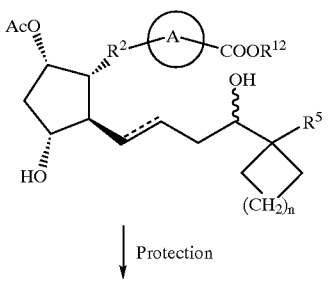
↓ Protection
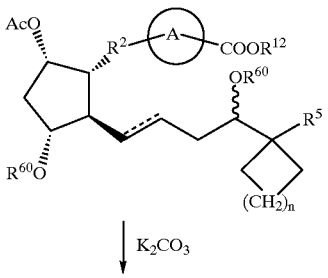
↓ K$_2$CO$_3$
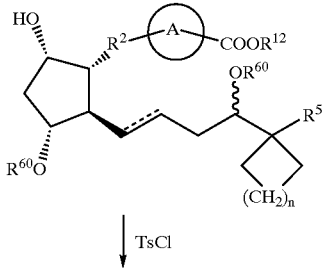
↓ TsCl
-continued
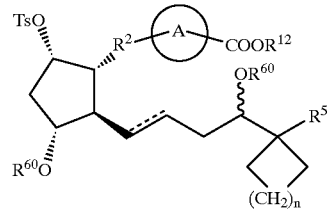
↓ halogenation
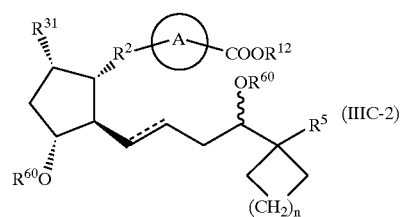
(IIIC-2)
Scheme (D)
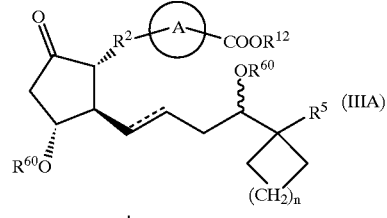
(IIIA)
↓ LiBH(sec-C$_4$H$_9$)$_3$
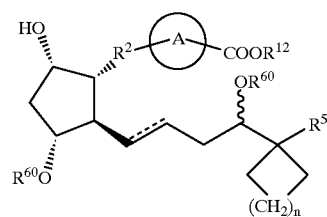
↓ HCOOH
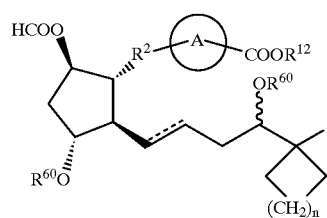
↓ NH$_3$ 41
-continued
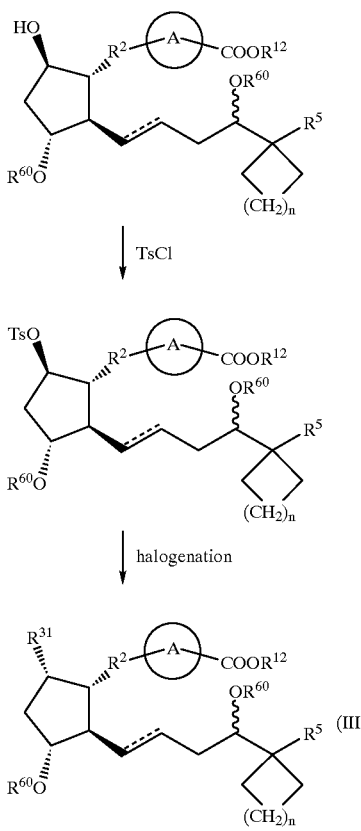
42
-continued
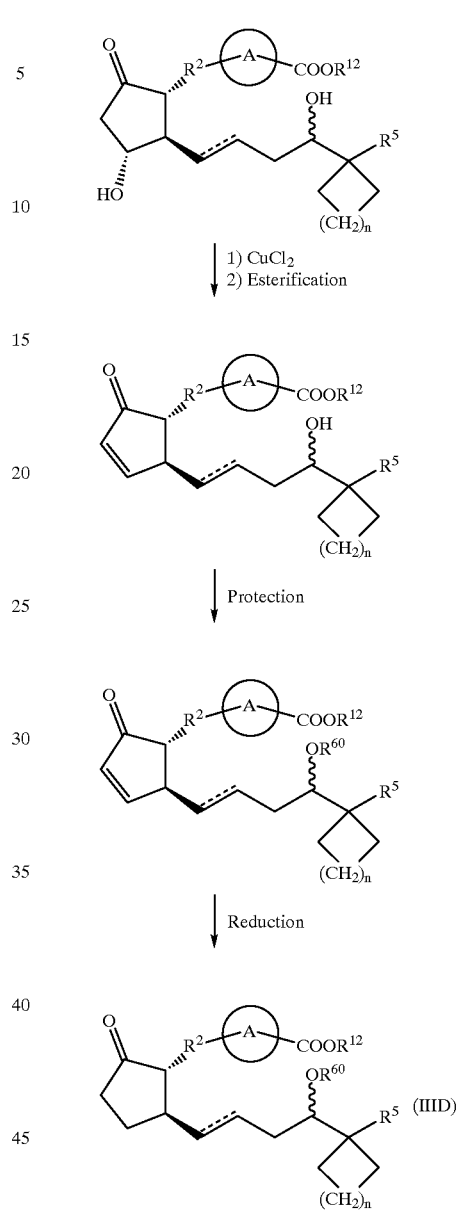
Scheme (E)
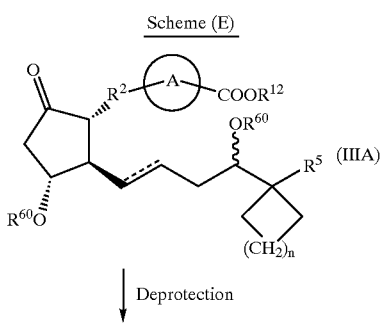
Scheme (F)
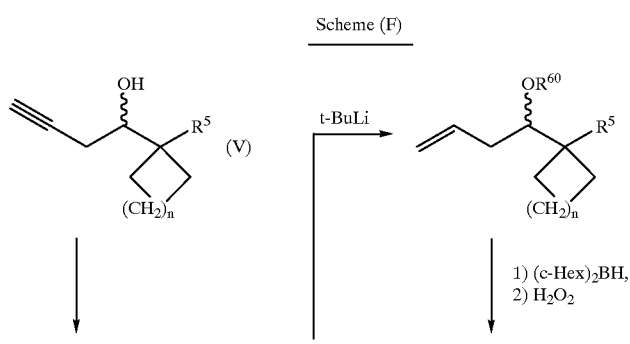

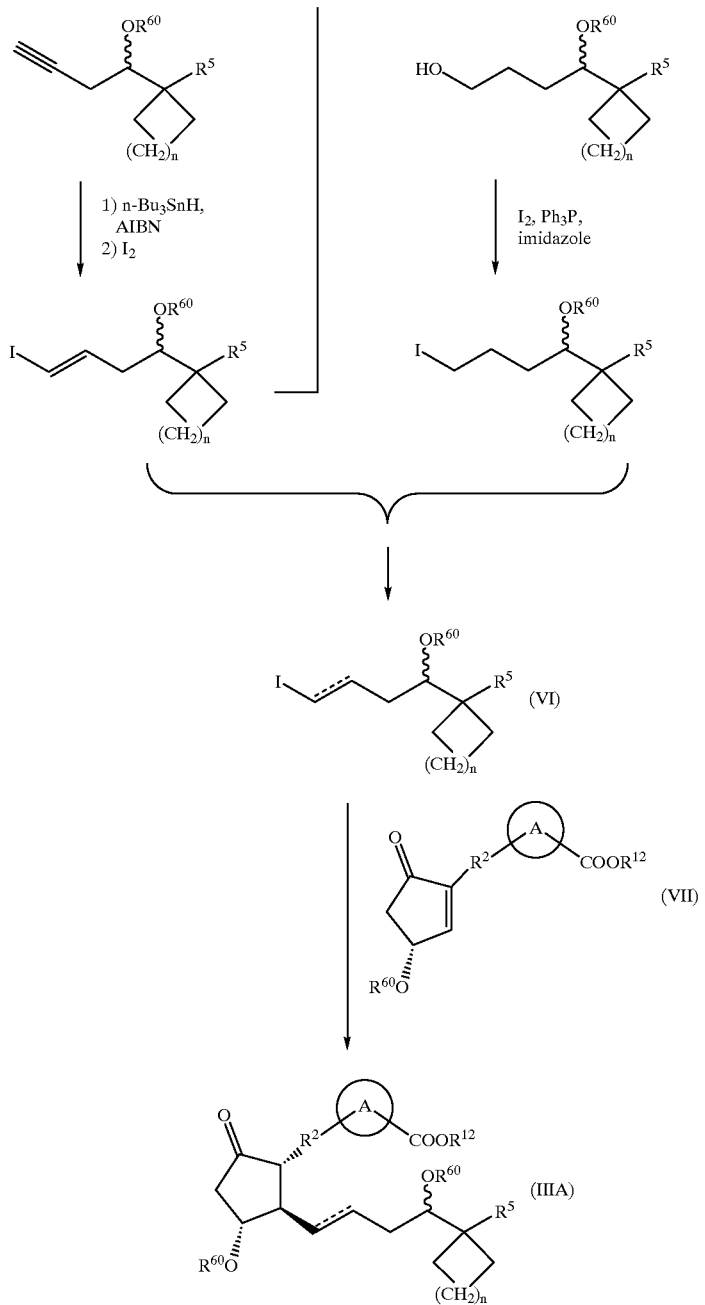
Scheme (G)
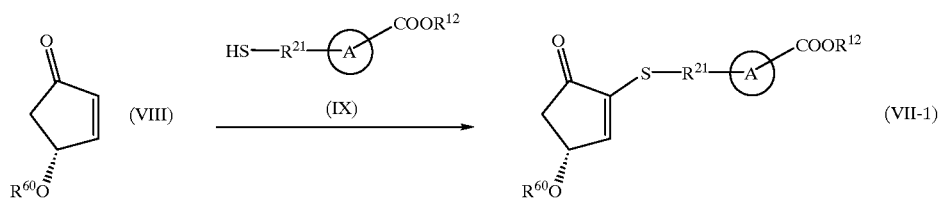

-continued
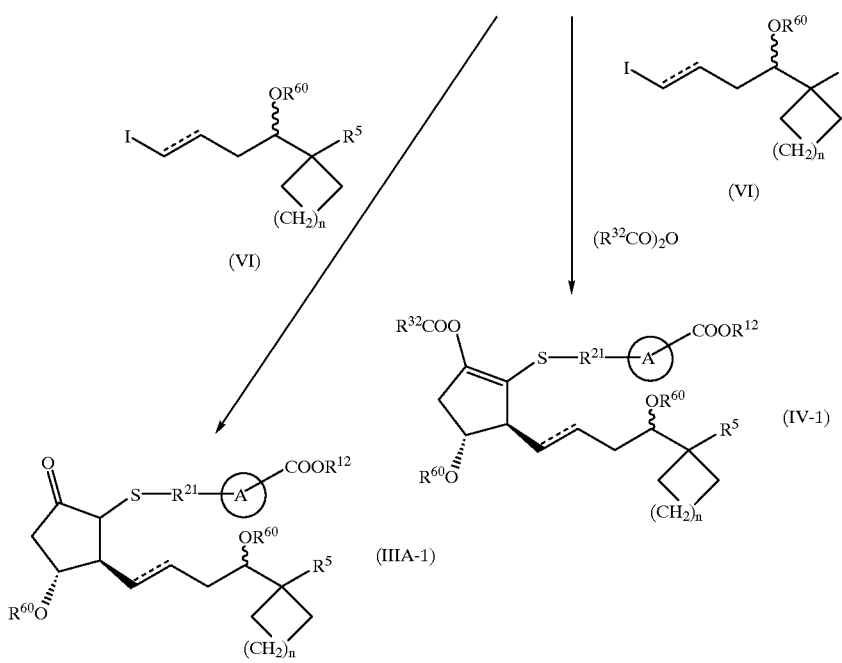
Scheme (H)
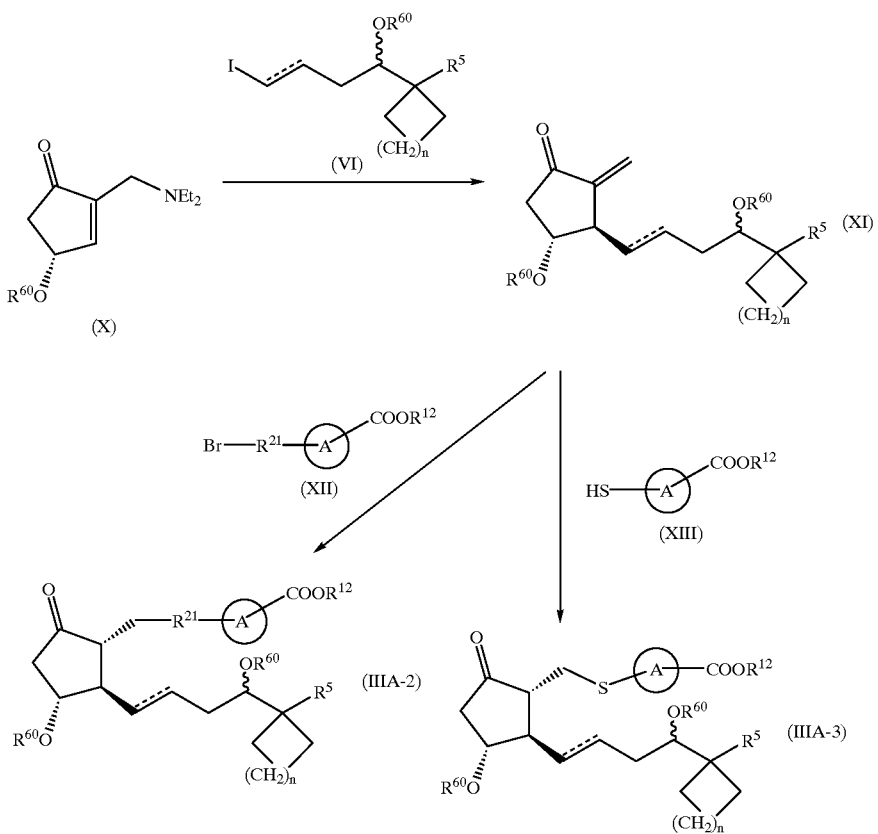

Scheme (J)
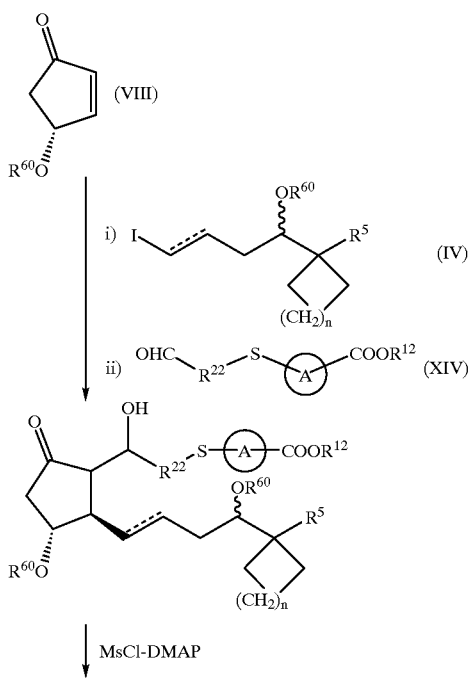
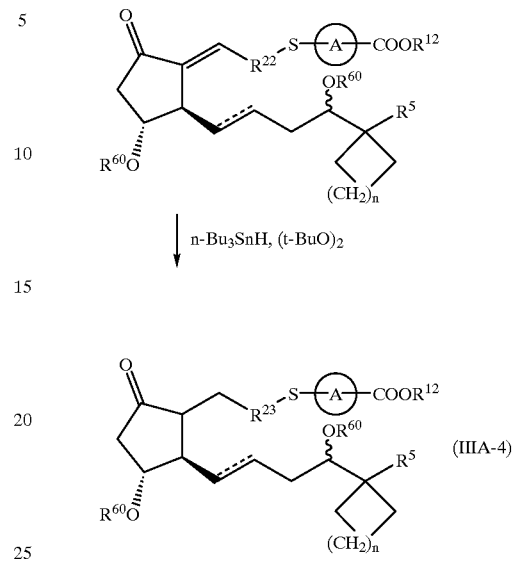
Scheme (K)
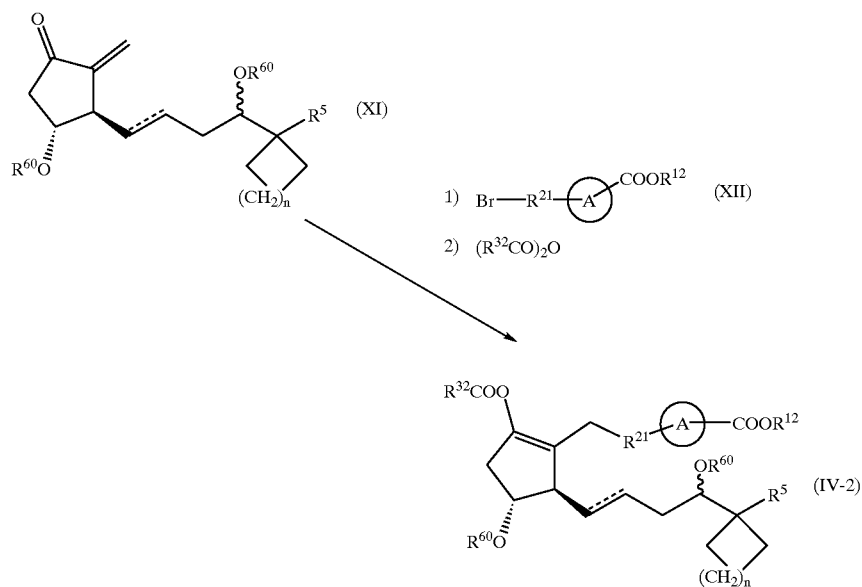

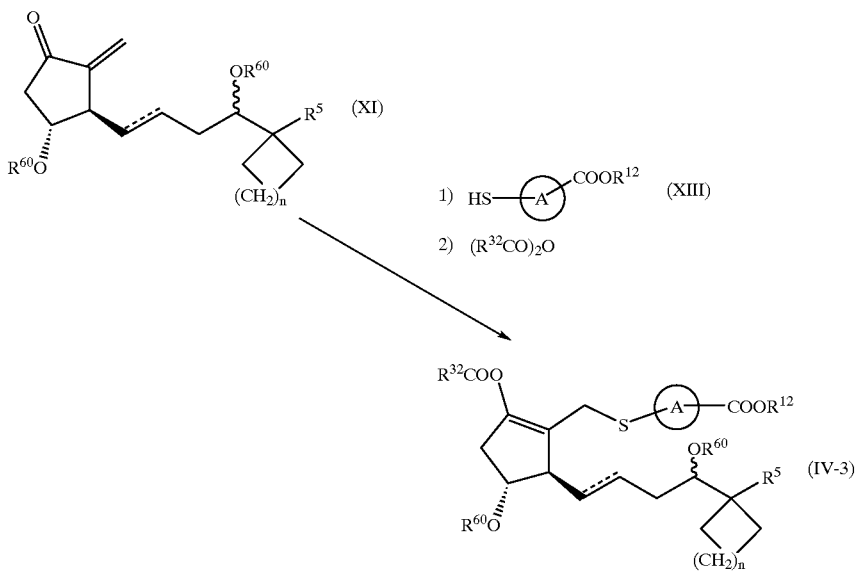

Each reaction in reaction Schemes described above is carried out by known methods. In the reaction Schemes described above, the compounds of formula (V), (VII), (VIII), (IX), (X), (XII), (XIII) and (XIV) as starting materials are known per se or may be prepared by known methods.

For example, among the compounds of formula (V), (4RS) -5,5-propanooct-1-yn-4-ol is a known compound described in the specification of JP54-115351.

Among the compounds of formula (X), (4R)-2-(diethylaminomethyl)-4-t-butyldimethylsilyloxy-2-cyclopenten-1-one is a known compound described in J. Org. Chem., 53, 5590-5592 (1988).

Among the compounds of formula (VIII), (4R)-4-t-butyldimethylsilyloxy-2-cyclopenten-1-one is a known compound described in J. Am. Chem. Soc., 110, No. 14, 4718-4726 (1988).

The other starting materials and reagents in the present invention are known per se or may be prepared by known methods.

In each reaction in the present specification, obtained products may be purified by conventional techniques. For example, purification maybe carried out by distillation under atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

[Pharmacological Activities]

The compounds of the present invention of formula (I) bind and act on EP2 receptor which is a subtype of $PGE_2$ receptor.

For example, the effects of the compounds of the present invention were confirmed by binding assay using expression cell of prostanoids receptor subtype.

(i) Binding Assay Using Expression Cell of Prostanoids Receptor Subtype

The preparation of membrane fraction was carried out according to the method of Sugimoto et. al., [J. Biol. Chem., 267, 6463–6466 (1992)], using expression CHO cell of the prostanoids receptor subtype (mouse EP1, EP2, EP3α, EP4).

The standard assay mixture containing membrane fraction (0.5 mg/ml) and [$^3$H]-$PGE_2$ (2.5 nm) in a final volume of 200 μl was incubated at room temperature for 1 hour. The reaction was terminated by addition of ice-cooled buffer (3 ml). The mixture was filtered through a GF/B glass filter under reduced pressure. The radioactivity associated with the filter was measured by liquid scintillation counter.

Kd and Bmax values were determined from Scatchard plots [Ann. N. Y. Acad. Sci., 51, 660 (1949)]. Non-specific binding was calculated as the binding in the presence of an excess (2.5 μM) of unlabeled $PGE_2$. In the experiment for competition of specific $^3$H-$PGE_2$ binding by the compounds of the present invention, 2.5 nM of $^3$H-$PGE_2$ and various concentrations of compounds of the present invention were added. The following buffer was used in all reactions.

Buffer: 10 mM potassium phosphate (pH 6.0), 1 mM EDTA, 10 mM $MgCl_2$, 0.1 M NaCl.

All the values shown are those obtained using the more polar stereoisomer of the exemplified compounds. The dissociation constant; i.e. Ki (μM) of each compound was calculated by the following equation.

$Ki=IC_{50}/(1+[C]/Kd))$

The results are shown in Table 21.

TABLE 21

| Example No. | Ki (μM) | | | |
|---|---|---|---|---|
| | $EP_1$ | $EP_2$ | $EP_{3α}$ | $EP_4$ |
| 2(a) | >10 | 0.0097 | >10 | >10 |
| 2(b) | >10 | 0.0061 | >10 | >10 |
| 5(b) | >10 | 0.019 | >10 | 1.50 |
| 5(d) | >10 | 0.002 | >10 | 0.31 |
| 9(c) | >10 | 0.0051 | >10 | >10 |

[Toxicity]

The toxicity of the compounds of the present invention is very low and therefore, it is confirmed that these compounds are safe for pharmaceutical use.

Industrial Applicability

The compounds of the present invention of formula (I) bind strongly and act on $PGE_2$ receptor, especially on EP2 subtype receptor and therefore are useful for prevention and/or treatment of immunological diseases (autoimmune diseases, organ transplantation etc.), asthma, abnormal bone formation, neuronal cell death, hepatopathy, abortion, premature birth or retina neuropathy of glaucoma etc.

Among the compounds of the present invention of formula (I), compounds which bind weakly on receptor subtypes except EP2 receptor and on other receptors for arachidonic acid cascade metabolites (thromboxane receptor, $PGI_2$ receptor etc.) do not express other effects and therefore it is probable that these compounds will be medical agents which have less side-effects.

For the purpose described above, the compounds of formula (I), non-toxic salts thereof, cyclodextrin clathrates thereof may be normally administered systemically or partially, by oral or parenteral administration.

The doses to be administered are determined depending upon age, body weight, symptom, the desired therapeutic effect, the route of administration, and the duration of the treatment etc. In the human adult, the doses per person per dose are generally from 1 μg to 100 mg, by oral administration, from once up to several times per day, and from 0.1 μg to 10 mg, by parenteral administration (preferred into vein) from once up to several times per day, or by continuous administration for from 1 hour to 24 hours per day into vein.

As mentioned above, the doses to be used depend upon various conditions. Therefore, there are cases in which doses lower than or greater than the ranges specified above may be used.

The compounds of the present invention may be administered in the form, for example, solidcompositions, liquid-compositions or other compositions for oral administration, or injections, liniments or suppositories etc. for parenteral administration.

Solid compositions for oral administration include compressed tablets, pills, capsules, dispersible powders, and granules. Capsules include hard capsules and soft capsules.

In these solid compositions for oral administration, one or more of the active compound(s) are formulated by conventional method as it is or after admixed with excipients (lactose, mannitol, glucose, microcrystalline cellulose, starch etc.), connecting agents (hydroxypropyl cellulose, polyvinyl pyrrolidone, magnesium metasilicate aluminate etc.), disintegrating agents (cellulose calcium glycolate etc.). lubricating agents (magnesiumstearateetc.), stabilizing agents, agents to assist dissolution (glutamic acid, aspartic acid etc.) etc. The tablets or pills may, if desired, be coated with coating agents (sugar, gelatin, hydroxypropyl cellulose, hydroxypropyl methyl cellulose phthalate etc.), or be coated with more than one films. Coating may include containment within capsules of absorbable materials such as gelatin.

Liquid compositions for oral administration include pharmaceutically acceptable aqueous solutions, suspensions, emulsions, syrups and elixirs etc. In such liquid compositions, one or more of the active compound(s) may be contained in diluent(s) commonly used in the art (purified water, ethanol or a mixture thereof etc.). These liquid compositions may also comprise wetting agents, suspending agents, emulsifying agents, sweetening agents, flavoring agents, perfuming agents and preserving agents, buffering agents etc.

Injections for parenteral administration include solutions, suspensions and solid injections which may be dissolved or suspended in solvents before use. Injections are prepared by dissolving, suspending or emulsifying one or more of the active compound(s) in solvents. Solvents include, for example, distilled water for injection and physiological salt solution, vegetable oil, propylene glycol, polyethylene glycol, alcohol such as ethanol and the combination thereof. These injections may include stabilizing agents, agents to assist dissolution (glutamic acid, aspartic acid, POLYSORBATE8O (registered trade mark) etc.), suspending agents, emulsifying agents, pain-removing agents, buffering agents, preserving agents etc. These are sterilized in the final scheme or are prepared by asepticism. Sterile solid compositions, such as freeze-dried composition, may be prepared, to sterilize or to solve in sterile distilled water for injection or other sterile solvents before use.

Other compositions for parenteral administration include liquids for external use, and ointment, endermic liniments, nhalants, spray compositions, suppositories for rectal dministration and pessaries for vaginal administration etc. hich comprise one or more of the active compound(s) and may be prepared by conventional methods.

Spray compositions may comprise stabilizing agents such as sodium sulfite hydride, isotonic buffers such as sodium chloride, sodium citrate or citric acid). The preparation of spray compositions, for example, is described in the U.S. Pat. No. 2,868,691 or No. 3,095,355 in detail.

REFERENCE EXAMPLES AND EXAMPLES

The following reference examples and examples are intended to illustrate, but do not limit, the present invention.

The solvents in parentheses show the developing or eluting solvents and the ratios of the solvents used are by volume in chromatographic separations. The solvents in parentheses in NMR show the solvents used in measurement. In the examples, TBS is t-butyldimethylsilyl.

Reference Example 1

(4RS)-4-t-Butyldimethylsilyloxy-5,5-propanooct-1-yne

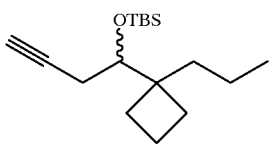

To the mixture solution of (4RS)-5,5-propanooct-1-yn-4-ol (4.0 g) and imidazole (4.9 g) in dimethylformamide (50 ml) was added t-butyldimethylsilyl chloride (5.4 g) under cooling with ice. The reaction mixture was stirred at 60° C. for 7 hours. The reaction was quenched by addition of water. The mixture was extracted with ethyl acetate. The extract was washed with water and a saturated aqueous solution of sodium chloride, dried over anhydrous magnesium sulfate and concentrated. The residue was purified by column chromatography on silica gel (hexane→hexane:ethyl acetate=10:1) to give the title compound (6.8 g) having the following physical data.

TLC: Rf 0.64 (hexane);

NMR (CDCl$_3$): δ 3.75 (1H, t, J=5.8 Hz), 2.28 (1H, ddd, J=17, 5.0, 2.5 Hz), 2.16 (1H, ddd, J=17, 6.0, 2.5 Hz), 2.10–1.94 (1H, m), 1.92 (1H, t, J=2.5 Hz), 1.90–1.20 (9H, m), 0.90 (3H, t, J=6.0 Hz), 0.89 (9H, s), 0.12 (3H, s), 0.07 (3H, s)

Reference Example 2

(1E, 4RS)-1-Iodo-4-t-butyldimethylsilyloxy-5,5-propanooct-1-ene

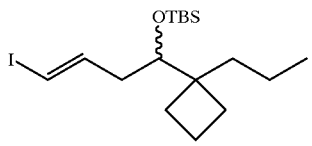

To the mixture of the compound prepared in reference example 1 (3.0 g) and tributyl tinhydride (3.7 ml) was added azobisisobutyronitrile (35 mg). The mixture was stirred at 80° C. for 1.5 hours. After the mixture was cooled to room temperature, to the mixture was added dropwise iodine (4.1 g) in methylene chloride (70 ml). The reaction mixture was stirred for 10 min. To the reaction mixture were added a saturated solution of sodium thiosulfate, ethyl acetate and a saturated aqueous solution of sodium chloride. The mixture was stirred, filtered, and the aqueous layer was extractedwith ethyl acetate. The organic layer was washed with a saturated aqueous solution of sodium chloride, dried over anhydrous magnesium sulfate and concentrated. The residue was purified by column chromatography on silica gel (hexane) to give the title compound (3.9 g) having the following physical data.

TLC: Rf 0.77 (hexane);

NMR (CDCl$_3$): δ 6.49 (1H, dt, J=14.5, 7.5 Hz), 5.97 (1H, d, J=14.5 Hz), 3.58 (1H, t, J=6.0 Hz), 2.20–1.20 (12H, m), 0.91 (3H, t, J=6.0 Hz), 0.91 (9H, s), 0.06 (3H, s), 0.05 (3H, s).

Reference Example 3

(3S,4R)-t-Butyldimethylsilyloxy-2-methylene-3-(4-t-butyldimethylsilyloxy-5,5-propanooct-1-enyl)cyclopentan-1-one

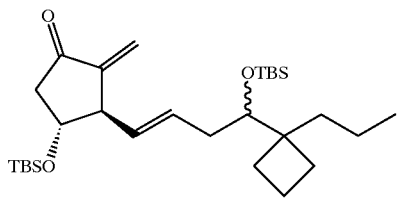

Under atmosphere of argon, to a stirred solution of (1E,4RS)-1-iodo-4-t-butyldimethylsilyloxy-5,5-propanooct-1-ene (302 mg, which was prepared in reference example 2) in diethyl ether (5 ml) at −78° C., was added t-butyllithium/pentane solution (0.87 ml, 1.64 M) dropwise, and the mixture was stirred for 45 minutes. To the mixture was added dropwise 2-thienyllithium cyanocuprate/THF solution (3.6 ml, 0.25 M) and the mixture was stirred for 20 minutes. To the solution was added (4R)-4-t-butyldimethylsilyloxy-2-diethylamino methylcyclopent-2-en-1-one (200 mg) dissolved in diethyl ether (3 ml), and the mixture was stirred warming from −78° C. to 0° C. for 1 hour. The reaction was terminated by addition of a saturated solution of ammonium chloride, and the mixture was extracted with ethyl acetate three times. The organic layer was washed with a saturated solution of ammonium chloride twice, a saturated solution of sodium chloride once, dried over anhydrous magnesium sulfate. The residue was purified by column chromatography on silica gel (Fuji Silysia BW-300 40 ml, ethyl acetate/hexane=0/1→1/50) to give the title compound (235 mg) having the following physical data as a sepia oil.

TLC: Rf 0.54 (ethyl acetate:hexane=1:15).

Reference Example 4

(11α, 13E)-9-Oxo-11,15-bis(t-butyldimethylsilyloxy)-17,17-propano-1,6- (p-phenylene)-2,3,4,5-tetranorprost-13-enoic Acid Methyl Ester

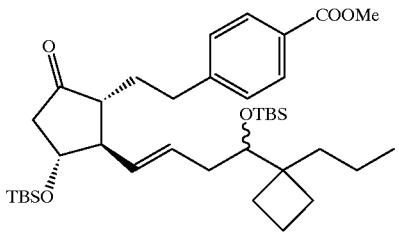

A. Preparation of Reformatosky Reagent

Under atmosphere of argon, to a suspension of zinc powder (654 mg) stirred in THF (0.5 ml) at room temperature, was added dropwise dibromoethane (15 ml), and the mixture was stirred at 60° C. for 2 minutes. The reaction mixture was cooled to room temperature, and trimethylsilyl chloride (22 μl) was added dropwise therein, and the mixture was stirred at 0° C. A solution of benzylbromide (1.14 g) in THF (4.5 ml) was added therein, and the mixture was stirred at 10° C. for 3 hours.

B. Preparation for cuprous reagent

Under atmosphere of argon, cuprous cyanide (896 mg) and lithium chloride (890 mg) were dissolved in THF (10 ml), and the mixture was stirred for 3 hours.

C. Michael Addition Reaction

Under atmosphere of argon, to a Reformatosky reagent (0.58 ml) stirred at −78° C., was added dropwise the cuprous reagent (0.72 ml). The reaction solution was stirred at −78° C. for 30minutes. Trimethylsilylchloride (66 μl) andthecompound prepared in reference example 3 (150 mg) in THF (2 ml) were added dropwise therein successively. The reaction solution was stirred at −78° C. for 1 hour and at −20° C. for 2 hours. The reaction was terminated by addition of a saturated solution of ammonium chloride, and the mixture was extracted with ethyl acetate three times. The organic layer was washed with water twice, with a saturated aqueous solution of sodium chloride once, and concentrated. The residue was dissolved in methanol/ether (2 ml+1 ml) mixed solvents, and the mixture was stirred at room temperature. Pyridinium p-toluenesulfonate (4 mg) was added therein, and the mixture was stirred at room temperature for 1 hour. The reaction was terminated by addition of a saturated aqueous solution of sodiumbicarbonate, and extracted with ethyl acetate three times. The organic layer was washed with water twice, with a saturated aqueous solution of sodium chloride once, and concentrated. The residue was purified by column chromatography on silica gel (Merck 7734 20 ml, ethyl acetate/hexane=1/20→1/5) to give the title compound (53 mg) having the following physical data as a colorless oil.

TLC: Rf 0.60 (ethyl acetate:hexane=1:5);

NMR (CDCl$_3$): δ 7.94 (2H, d, J=8.5 Hz), 7.23 (2H, d, J=8.5 Hz), 5.80–5.50 (1H, m), 5.40–5.20 (1H, m), 4.96 (1H, dd, J=7.5, 2.5 Hz), 3.70 (3H, s), 3.57 (1H, t, J=5.0 Hz), 2.90–1.10 (20H, m), 1.00–0.75 (21H, m), 0.10–0.00 (6H, m).

Example 1
(11α,13E)-9-Oxo-11,16-dihydroxy-17,17-propano-1,6-(p-phenylene)-2,3,4,5-tetranorprost-13-enoic Acid Methyl Ester

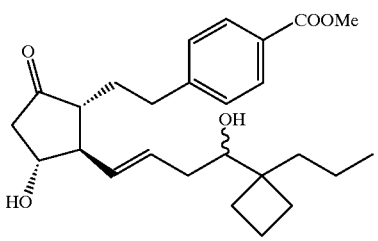

Under atmosphere of argon, to a solution of the compound prepared in reference example 4 (53 mg) in acetonitrile (2 ml) stirred at 0° C., was added an aqueous solution of hydrofluoric acid (0.2 ml, 48%), and the mixture was stirred for 3 hours. The reaction was terminated by addition of water, and the solution was extracted with ethyl acetate three times. The organic layer was washed with water twice, with a saturated aqueous solution of sodium chloride once, and concentrated. The residue was purified by column chromatography on silica gel (Merck Lobar prepacked column size A, ethyl acetate/hexane=1/1) to give the title compounds (less polar isomer (12 mg) and more polar isomer (11.5 mg)) having the following physical data as a colorless oil respectively.

Less Polar

TLC: Rf 0.28 (ethyl acetate:hexane=1:1);

NMR (CDCl$_3$): δ 7.94 (2H, d, J=8.5 Hz), 7.24 (2H, d, J=8.5 Hz), 5.74 (1H, dt, J=15.5, 7.0 Hz), 5.43 (1H, dd, J=15.5, 8.5 Hz), 4.06 (1H, q, J=9.0 Hz), 3.90 (3H, s), 3.58 (1H, dd, J=9.5, 3.0 Hz), 3.00–2.80 (3H, m), 2.50–1.20 (19H, m), 0.95 (3H, t, J=6.5 Hz).

More Polar

TLC: Rf 0.22 (ethyl acetate:hexane=1:1);

NMR (CDCl$_3$): δ 7.94 (2H, d, J=8.5 Hz), 7.24 (2H, d, J=8.5 Hz), 5.69 (1H, ddd, J=15.0, 9.0, 5.0 Hz), 5.37 (1H, dd, J=15.0, 9.5 Hz), 4.03 (1H, q, J=8.0 Hz), 3.90(3H, S), 3.56 (1H, dd, J=10.0, 2.5 Hz), 3.00–2.60 (3H, m), 2.50–1.20 (19H, m), 0.94 (3H, t, J=7.0 Hz).

Example 1(a)–1(d)

By the same procedure as reference example 1, 2, 3, 4 and example 1, the compounds having the following physical data were obtained.

Example 1(a)
(11α,13E)-9-Oxo-11,16-dihydroxy-17,17-propano-1,6-(p-phenylene)-2,3,4,5-tetranorprost-13,19-dienoic Acid Methyl Ester

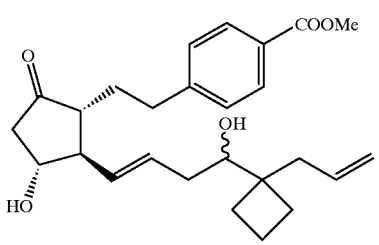

Less Polar

TLC: Rf 0.42 (hexane:ethyl acetate=1:2);

NMR (CDCl$_3$): δ 7.94 (2H, d, J=8.2 Hz), 7.25 (2H, d, J=8.2 Hz), 5.96 (1H, ddt, J=17.0, 10.0, 7.2 Hz), 5.74 (1H, dt, J=15.4, 6.8 Hz), 5.42 (1H, dd, J=15.4, 8.6 Hz), 5.20–5.05 (2H, m), 4.15–3.98 (1H, m), 3.90 (3H, s), 3.59 (1H, dd, J=9.5, 2.7 Hz), 2.90–2.65 (3H, m), 2.60–1.60 (17H, m).

More Polar

TLC: Rf 0.36 (hexane:ethyl acetate=1:2);

NMR (CDCl$_3$): δ 7.94 (2H, d, J=8.2 Hz), 7.24 (2H, d, J=8.2 Hz), 5.95 (1H, ddt, J=17.0, 10.0, 7.2 Hz), 5.69 (1H, ddd, J=15.0, 8.6, 5.4 Hz), 5.37 (1H, dd, J=15.0, 8.6 Hz), 5.20–5.05(2H, m), 4.10–3.95 (1H, m), 3.90 (3H, s), 3.57 (1H, dd, J=10.2, 2.2 Hz), 2.90–2.65 (3H, m), 2.45–1.55 (17H, m).

Example 1(b)
(11α,13E)-9-Oxo-11,16-dihydroxy-17,17-propano-19,20-methano-1,6-(p-phenylene)-2,3,4,5-tetranorprost-13-enoic Acid Methyl Ester

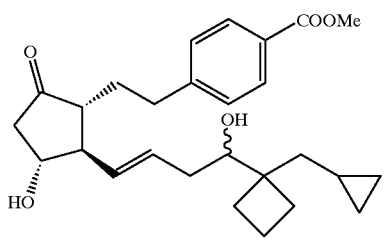

More Polar

TLC: Rf 0.56 (hexane ethyl:acetate=1:2);

NMR (CDCl$_3$): δ 7.94 (2H, d, J=8.3 Hz), 7.24 (2H, d, J=8.3 Hz), 5.69 (1H, ddd, J=15, 9.1, 5.5 Hz), 5.36 (1H, dd, J=15, 8.7 Hz), 4.02 (1H, m), 3.90 (3H, s), 3.69 (1H, dd, J=10, 1.4 Hz), 2.78 (3H, m), 2.56–1.63 (13H, m), 1.51 (1H, dd, J=14, 6.6 Hz), 1.38 (1H, dd, J=14, 6.2 Hz), 0.77 (1H, m), 0.50 (2H, m), 0.11 (2H, m).

Example 1(c)
(11α,13E)-9-Oxo-11,16-dihydroxy-17,17-propano-19-methyl-1,6 -(p-phenylene)-2,3,4,5-tetranorprost-13-enoic Acid Methyl Ester

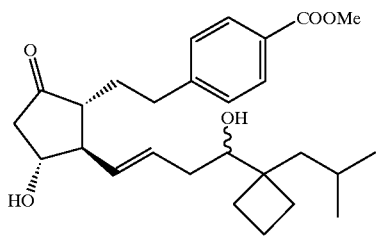

More Polar

TLC: Rf 0.64 (hexane:ethyl acetate=1:2);

NMR (CDCl$_3$): δ 7.94 (2H, d, J=8.2 Hz), 7.24 (2H, d, J=8.2 Hz). 5.69 (1H, ddd, J=15, 9.4, 5.3 Hz), 5.38 (1H, dd, J=15, 8.7 Hz), 4.03 (1H, m), 3.90 (3H, s), 3.64 (1H, dd, J=10, 1.5 Hz), 2.77 (3H, m), 2.58–1.63 (14H, m), 1.55 (1H, dd, J=14, 6.6 Hz), 1.34 (1H, dd, J=14, 6.4 Hz), 0.92 (6H, d, J=6.4 Hz).

Example 1(d)

(11α,13E)-9-Oxo-11,16-dihydroxy-17,17-propano-1,6-(p-phenylene)-2,3,4,5,20-pentanorprost-13-enoic Acid Methyl Ester

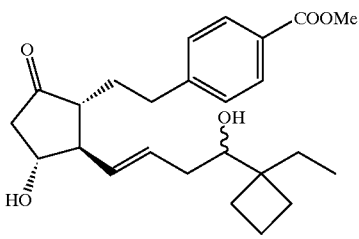

Less Polar

TLC: Rf 0.49 (ethyl acetate:hexane=3:2);

NMR (CDCl$_3$): δ 7.94 (2H, d, J=8.5 Hz), 7.25 (2H, d, J=8.5 Hz), 5.73 (1H, dt, J=15.5, 6.5 Hz), 5.43 (1H, dd, J=15.5, 8.5 Hz), 4.06 (1H, q, J=8.0 Hz), 3.90 (3H, s), 3.59 (1H, dd, J=9.5, 2.5 Hz), 3.00–2.60 (4H, m), 2.50–1.30 (14H, m), 0.93 (3H, t, J=7.5 Hz).

More Polar

TLC: Rf 0.43 (ethyl acetate:hexane=3:2);

NMR (CDCl$_3$): δ 7.94 (2H, d, J=8.0 Hz), 7.24 (2H, d, J=8.0 Hz), 5.69 (1H, ddd, J=15.0, 9.0, 5.5 Hz), 5.37 (1H, dd, J=15.0, 9.0 Hz), 4.03 (1H, q, J=8.5 Hz), 3.90 (3H, s), 3.57 (1H, dd, J=10.0, 2.0 Hz), 2.95–2.60 (3H, m), 2.50–1.30 (15H, m), 0.93 (3H, t, J=7.5 Hz).

Example 2

(11α,13E)-9—Oxo-11,16-dihydroxy-17,17-propano-1,6-(p-phenylene)-2,3,4,5-tetranorprost-13-enoic Acid

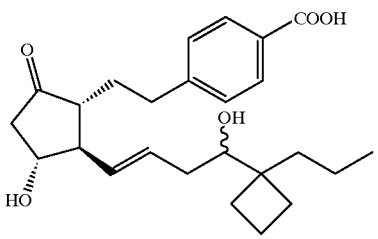

To a suspension of the compound prepared in example 1 (10 mg, less polar) stirred in DMSO-phosphoric acid buffer (1 ml+1 ml) at room temperature, PLE (porcine liver esterase, 100 μl) was added, and the mixture was stirred at room temperature for 9 hours. The reaction was quenched by addition of a saturated aqueous solution of ammonium chloride, and the mixture was extracted by ethyl acetate. The organic layer was washed with brine/1N hydrochloric acid twice, with brine once, and dried over anhydrous magnesium sulfate, and concentrated. The residue was purified by column chromatography on silica gel (WAKO-C200 5 ml, ethyl acetate/hexane=1/1→1/0 to give the title compound (7 mg, less polar) having the following physical data as a colorless oil.

TLC: Rf 0.39 (ethyl acetate:hexane=3:1);

NMR (CDCl$_3$): δ 7.98 (2H, d, J=8.0 Hz), 7.26 (2H, d, J=8.0 Hz), 5.75 (1H, dt, J=15.5, 6.5 Hz), 5.45 (1H, dd, J=15.5, 8.0 Hz), 4.08 (1H, q, J=9.0 Hz), 3.61 (1H, dd, J=10, 3.0 Hz), 3.00–2.60 (3H, m), 2.50–1.20 (19H, m), 0.95 (3H, t, J=7.0 Hz).

By the same procedure as described above, using the compound prepared in example 1 (more polar), the compound having the following physical data was obtained.

TLC: Rf 0.32 (hexane: ethyl acetate=1:3);

NMR (CDCl$_3$): δ 7.99 (2H, d, J=8.2 Hz), 7.27 (2H, d, J=8.2 Hz), 5.71 (1H, ddd, J=15.4, 8.4, 5.2 Hz), 5.40 (1H, dd, J=15.4, 8.6 Hz), 4.15–3.95 (1H, m), 3.59 (1H, dd, J=10.0, 2.2 Hz), 3.00–1.50 (3H, br), 2.90–2.65 (3H, m), 2.50–1.20 (17H, m), 0.95 (3H, t, J=6.8 Hz).

Example 2(a)–2(d)

By the same procedure as example 2, using the compounds prepared in example 1(a)–1(d), the compounds having the following physical data were obtained.

Example 2(a)

(11α,13E)-9-Oxo-11,16-dihydroxy-17,17-propano-1,6-(p-phenylene)-2,3,4,5-tetranorprost-13,19-dienoic Acid

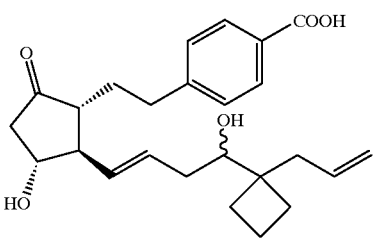

More Polar

TLC: Rf 0.33 (hexane:ethyl acetate:acetic acid=1:2:0.03);

NMR (CDCl$_3$): δ 7.99 (2H, d, J=8.2 Hz), 7.26 (2H, d, J=8.2 Hz), 5.95 (1H, ddt, J=17.0, 10.0, 7.4 Hz), 5.69 (1H, ddd, J=15.0, 8.6, 5.2 Hz), 5.38 (1H, dd, J=15.0, 9.0 Hz), 5.20–5.05 (2H, m), 5.00–3.00 (3H, br), 4.15–3.95 (1H, m), 3.59 (1H, dd, J=10.2, 2.2 Hz), 2.95–2.65 (3H, m), 2.50–1.65 (15H, m).

Example 2(b)

(11α,13E)-9-Oxo-11,16-dihydroxy-17,17-propano-19,20-methano-1,6-(p-phenylene)-2,3,4,5-tetranorprost-13-enoic Acid

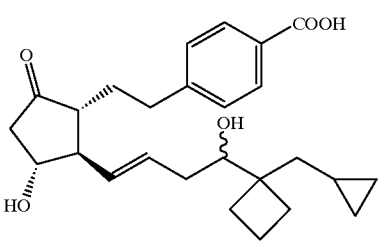

More Polar

TLC: Rf 0.44 (hexane:ethyl:acetate=1:4);

NMR (CDCl$_3$): δ 7.99 (2H, d, J=8.3 Hz), 7.25 (2H, d, J=8.3 Hz), 5.71 (1H, ddd, J=15, 9.1, 5.3 Hz), 5.38 (1H, dd, J=15, 8.7 Hz), 4.19 (3H, br), 4.05 (1H, m), 3.71 (1H, dd, J=9.4, 1.5 Hz), 2.78 (3H, m), 2.31 (3H, m), 2.17–1.61 (10H, m), 1.52 (1H, dd, J=14, 6.8 Hz), 1.38 (1H, dd, J=14, 6.4 Hz), 0.78 (1H, m), 0.51 (2H, m), 0.11 (2H, m).

Example 2(c)
(11α,13E)-9-Oxo-11,16-dihydroxy-17,17-propano-19-methyl -1,6-(p-phenylene)-2,3,4,5-tetranorprost-13-enoic Acid

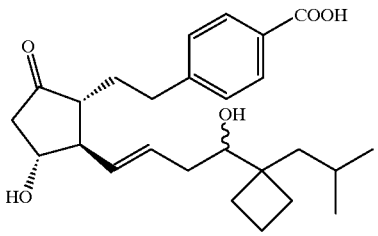

More Polar

TLC: Rf 0.52 (hexane:ethyl acetate=1:4); NMR (CDCl₃): δ 7.99 (2H, d, J=8.4 Hz), 7.25 (2H, d, J=8.4 Hz), 5.71 (1H, ddd, J=15, 9.4, 5.4 Hz), 5.40 (1H, dd, J=15, 9.0 Hz), 4.48 (3H, br), 4.06 (1H, m), 3.69 (1H, dd, J=9.0, 1.4 Hz), 2.78 (3H, m), 2.50–1.62 (14H, m), 1.56 (1H, dd, J=14, 6.7 Hz), 1.35 (1H, dd, J=14, 6.3 Hz), 0.92 (6H, d, J=6.2 Hz).

Example 2(d)
(11α,13E)-9-Oxo-11,16-dihydroxy-17,17-propano-1,6-(p-phenylene)-2,3,4,5,20-pentanorprost-13-enoic Acid

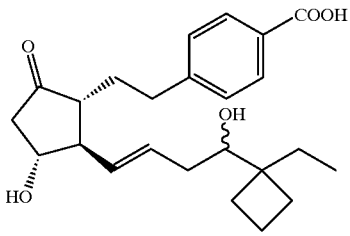

More Polar

TLC: Rf 0.39 (ethyl acetate:hexane:acetic acid 9:3:0.1);
NMR (CDCl₃): δ 7.99 (2H, d, J=8.0 Hz), 7.26 (2H, d, J=8.0 Hz), 5.70 (1H, ddd, J=14.0, 8.5, 5.0 Hz), 5.39 (1H, dd, J=14.0, 9.0 Hz), 4.05 (1H, q, J=8.0 Hz), 3.60 (1H, dd, J=10, 2.0 Hz), 2.90–2.65 (3H, m), 2.50–2.15 (3H, m), 2.15–1.30 (14H, m), 0.93 (3H, t, J=7.5 Hz).

Reference Example 5
(4R)-2-(4-Methoxycarbonylphenylmethylthio)-4-t-butyldimethylsilyloxycyclopent-2-en-1-one

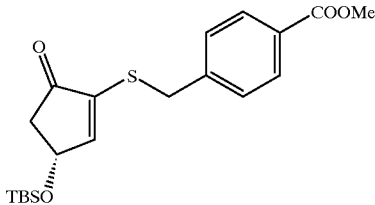

To a solution of 4-(t-butyldimethylsilyloxy) cyclopent-2-en-1-one (466 mg) in methanol (5 ml), was added dropwise an aqueous solution of hydrogen peroxide (1.00 ml, 31%) under cooling with ice, and the mixture was stirred for 15 minutes. To the reaction solution was added a saturated aqueous solution of ammonium chloride. The mixture was extracted with ethyl acetate twice, and the combined organic layer was washed with a saturated aqueous solution of sodium thiosulfate, with a saturated aqueous solution of sodium chloride, successively. The solution was dried over magnesium sulfate and concentrated. To a solution of the crude product in chloroform (15 ml), alumina (5 g) and 4-mercaptomethyl methyl benzoate (3.43 g) were added and the mixture was stirred for 15 hours. The reaction solution was filtered, and the filtrate was concentrated in vacuo to give a crude product. The crude product was purified by column chromatography on silica gel (ethyl acetate - hexane) to give the title compound (611 mg) having the following physical data.

TLC: Rf 0.38 (hexane:ethyl acetate=1:1);
NMR (CDCl₃): δ 8.00 (2H, d, J=8.0 Hz), 7.42 (2H, d, J=8.0 Hz), 6.83 (1H, d, J=3.0 Hz), 4.87 (1H, m), 4.15 (1H, d, J=13.0 Hz), 4.07 (1H, d, J=13.0 Hz), 3.90 (3H, s), 2.81 (1H, dd, J=19.0, 6.0 Hz), 2.33 (1H, dd, J=19.0, 2.0 Hz), 0.90 (9H, s), 0.06 (6H, s).

Reference Example 6
(11α,8Z, 13E)-9-Acetyloxy-11,16-bis(t-butyldimethylsilyloxy)-17,17-propano-7-thia-1,6-(p-phenylene)-2,3,4,5,20-pentanorprost-8,13-dienoic Acid Methyl Ester

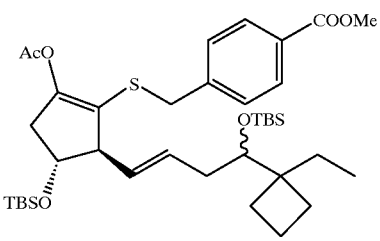

Under atmosphere of argon, to a solution of 1-iodo-4-t-butyldimethylsilyloxy-5,5-propano-1-heptene (400 mg) in diethyl ether (10 ml) stirred at -78° C., t-butyllithium/pentane solution (1.24 ml, 1.64 M) was added dropwise slowly, and the mixture was stirred at -78° C. for 45 minutes. Lithium cyano thiophenyl cuprate/THF solution (4.8 ml, 0.25 M) was added therein, and the mixture was stirred for 20 minutes. To the mixture, a solution of the compound prepared in reference example 5 (362 mg) in diethyl ether (6 ml) was added dropwise slowly, and warmed from -78° C. to -10° C. over a period of 1.5 hours. To the reaction solution, acetic anhydride (0.13 ml) was added dropwise, and the mixture was stirred at a temperature from -10° C. to 0° C. for 15 minutes. The reaction was quenched by addition of a saturated aqueous solution of ammonium chloride, and the mixture was extracted with ethyl acetate three times. The organic layer was washed with a saturated aqueous solution of ammonium chloride twice, with brine once, dried over anhydrous magnesium sulfate, and concentrated. The residue was purified by column chromatography on silica gel (Merck Kiesel gel 7734, 50 ml, ethyl acetate/hexane=1/15) to give the title compound (422 mg) having the following physical data as a light yellow oil.

TLC: Rf 0.31 (ethyl acetate:hexane=1:10);
NMR (CDCl₃): δ 7.93 (2H, d, J=8.5 Hz), 7.32 (2H, d, J=8.5 Hz), 5.70–5.50 (1H, m), 5.30–5.10 (1H, m), 4.10–4.00 (1H, m), 3.89 (3H, s), 3.85–3.78 (2H, m), 3.57 (1H, t, J=5.0 Hz), 3.10–3.00 (1H, m), 2.95–2.80 (1H, m), 2.42–2.30 (1H, m), 2.20–2.10 (2H, m), 2.07 (3H, s), 2.00–1.30 (5H, m), 1.00–0.90 (3H, s), 0.89 (9H, s), 0.84 (9H, s), 0.10–0.00 (6H, m), 0.00 (6H, s).

Example 3

(11α,8Z, 13E)-9-Acetyloxy-11,16-dihydroxy-17,17-propano-7-thia-1,6-(p-phenylene)-2,3,4,5,20-pentanorprost-8,13-dienoic acid Methyl Ester

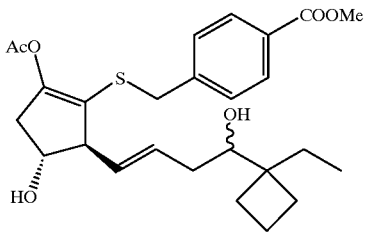

By the same procedure as example 1, using the compound prepared in reference example 6, the compounds having the following physical data were obtained.

Less Polar
TLC: Rf 0.59 (ethyl acetate:hexane=3:2);
NMR (CDCl$_3$): δ 7.98 (2H, d, J=8.5 Hz), 7.37 (2H, d, J=8.5 Hz), 5.55 (1H, ddd, J=15.0, 8.5, 6.0 Hz), 5.26 (1H, dd, J=15.0, 9.0 Hz), 4.20–4.05 (1H, m), 3.91 (3H, s), 3.86 (2H, s), 3.49 (1H, dd, J=10.0, 2.5 Hz), 3.10–3.00 (1H, m), 2.92 (1H, ddd, J=16.5, 7.0, 1.0 Hz), 2.49 (1H, ddd, J=16.5, 12.5, 1.0 Hz), 2.30–1.30 (12H, m), 2.15 (3H, s), 0.92 (3H, t, J=7.5 Hz).

More Polar
TLC: Rf 0.52 (ethyl acetate:hexane=3:2);
NMR (CDCl$_3$): δ 7.97 (2H, d, J=8.0 Hz), 7.37 (2H, d, J=8.0 Hz), 5.61 (1H, ddd, J=15.0, 8.5, 7.0 Hz), 5.35 (1H, dd, J=15.0, 8.5 Hz), 4.20–4.05 (1H, m), 3.91 (3H, s), 3.86 (2H, s), 3.54 (1H, dd, J=9.0, 3.0 Hz), 3.08 (1H, dd, J=8.5, 3.0 Hz), 2.92 (1H, ddd, J=16.0, 6.5, 1.5 Hz), 2.46 (1H, ddd, J=16.0, 4.0, 1.5 Hz), 2.30–2.10 (1H, m), 2.15 (3H, s), 2.10–1.30 (10H, m), 0.92 (3H, t, J=7.5 Hz).

Example 3(a)–3(d)

By the same procedure as reference example 1, 2, 3, 4 and example 3, the compounds having the following physical data were obtained.

Example 3(a)

(11α,8Z, 13E)-9-Acetyloxy-11,16-dihydroxy-17,17-propano-7-thia-1,6-(p-phenylene)-2,3,4,5-tetranorprost-8,13-dienoic Acid Methyl Ester

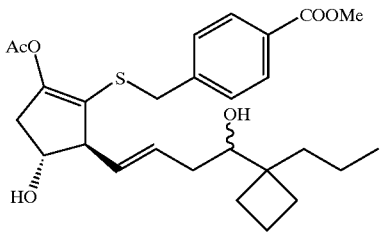

Less Polar
TLC Rf 0.55 (ethyl acetate:hexane=3 2);
NMR (CDCl$_3$): δ 7.97 (2H, d, J=8.0 Hz), 7.37 (2H, d, J=8.0 Hz), 5.55 (1H, ddd, J=15.0, 8.5, 5.5 Hz), 5.26 (1H, dd, J=15.0, 9.0 Hz), 4.20–4.05 (1H, m), 3.91 (3H, s), 3.86 (2H, s), 3.49 (1H, dd, J=10.0, 2.0 Hz), 3.07 (1H, dd, J=9.0, 4.0 Hz), 2.92 (1H, ddd, J=16.5, 7.0, 2.0 Hz), 2.49 (1H, ddd, J=16.5, 4.0, 2.0 Hz), 2.40–1.20 (15H, m), 2.15 (3H, s), 0.94 (3H, t, J=6.5 Hz).

More Polar
TLC: Rf 0.50 (ethyl acetate:hexane=3:2);
NMR (CDCl$_3$): δ 7.97 (2H, d, J=8.0 Hz), 7.36 (2H, d, J=8.0 Hz), 5.56 (1H, ddd, J=15.5, 8.0, 5.5 Hz), 5.36 (1H, dd, J=15.5, 8.5 Hz), 4.20–4.05 (1H, m), 3.90 (3H, s), 3.88 (2H, s), 3.52 (1H, dd, J=10.0, 2.5 Hz), 3.09 (1H, dd, J=8.5, 3.5 Hz), 2.90 (1H, ddd, J=16.5, 7.0, 2.0 Hz), 3.00–2.60(1H, brs), 2.46 (1H, ddd, J=16.0, 4.0, 1.5 Hz), 2.25–2.15 (1H, m), 2.15 (3H, s), 2.10–1.20 (13H, m), 0.94 (3H, t, J=6.5 Hz).

Example 3(b)

(11α,8Z, 13E)-9-Acetyloxy-11,16-dihydroxy-17,17-propano-7-thia-1,6-(p-phenylene)-2,3,4,5-tetranorprost-8,13,19-trienoic Acid Methyl Ester

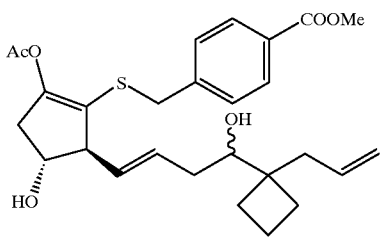

Less Polar
TLC Rf 0.59 (ethyl acetate:hexane=3:2);
NMR (CDCl$_3$): δ 7.98 (2H, d, J=8.5 Hz), 7.38 (2H, d, J=8.5 Hz), 6.06–5.82 (1H, m), 5.54 (1H, ddd, J=15.5, 8.5, 6.0 Hz), 5.26 (1H, dd, J=15.5, 8.5 Hz), 5.18–5.04 (2H, m), 4.20–4.05 (1H, m), 3.91 (3H, s), 3.86 (2H, s), 3.50 (1H, dd, J=10.0, 2.5 Hz), 3.10–3.00 (1H, m), 2.92 (1H, ddd, J=16.5, 7.0, 1.5 Hz), 2.60–1.30 (13H, m), 2.15 (3H, s).

More Polar
TLC: Rf 0.52 (ethyl acetate:hexane=3:2);
NMR (CDCl$_3$): δ 7.97 (2H, d, J=8.5 Hz), 7.36 (2H, d, J=8.5 Hz), 6.06–5.82 (1H, m), 5.62 (1H, ddd, J=15.5, 8.5, 5.5 Hz), 5.35 (1H, dd, J=15.0, 8.5 Hz), 5.20–4.94 (2H, m), 4.20–4.05 (1H, m), 3.90 (3H, s), 3.88 (2H, s), 3.53 (1H, dd, J=10.0, 2.5 Hz), 3.08 (1H, dd, J=6.0, 1.5 Hz), 2.91 (1H, ddd, J=16.5, 7.0, 2.0 Hz), 2.55–1.30 (13H, m), 1.26 (3H, t, J=7.0 Hz).

Example 3(c)

(11α,8z, 13E)-9-Acetyloxy-11,16-dihydroxy-19-methyl-17,17-propano-7-thia-1,6-(p-phenylene)-2,3,4,5-tetranorprost-8,13-dienoic Acid Methyl Ester

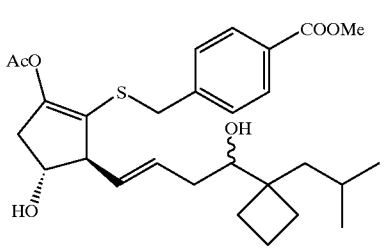

Less Polar
TLC Rf 0.45 (ethyl acetate hexane=1:1);
NMR (CDCl$_3$): δ 7.98 (2H, d, J=8.5 Hz), 7.38 (2H, d, J=8.5 Hz), 5.56 (1H, ddd, J=14.5, 8.5, 6.0 Hz), 5.27 (1H, dd, J=14.5, 9.0 Hz), 4.20–4.05 (1H, m), 3.91 (3H, s), 3.88 (2H, s), 3.58 (1H, dd, J=10.0, 2.0 Hz), 3.14–3.00 (1H, m), 2.92 (1H, ddd, J=16.0, 6.0, 1.5 Hz), 2.49 (1H, ddd, J=16.0, 4.0, 1.5 Hz), 2.35–2.20 (1H, m), 2.20–1.50 (10H, m), 2.15 (3H, s), 1.33 (1H, dd, J=14.0, 6.0 Hz), 0.93 (3H, d, J=6.5 Hz), 0.93 (3H, d, J=6.5 Hz).

More Polar

TLC: Rf 0.38 (ethyl acetate:hexane=1:1);

NMR (CDCl3): δ 7.97 (2H, d, J=8.0 Hz), 7.37 (2H, d, J=8.0 Hz), 5.75–5.55 (1H, m), 5.38 (1H, dd, J=15.5, 8.0 Hz), 4.20–4.05 (1H, m), 3.91 (3H, s), 3.88 (2H, s), 3.62 (1H, d, J=10.0 Hz), 3.09 (1H, d, J=8.5 Hz), 2.93 (1H, ddd, J=16.5, 6.5, 1.5 Hz), 2.46 (1H, dd, J=16.5, 3.5 Hz), 2.40–2.20 (2H, m), 2.16 (3H, s), 2.15–1.50 (9H, m), 1.55 (1H, dd, J=14.5, 7.0 Hz), 1.33 (1H, dd, J=14.5, 6.5 Hz), 0.91 (6H, d, J=6.5 Hz).

Example 3(d)

(11α,8Z, 13E)-9-Acetyloxy-11,16-dihydroxy-17,17-propano-19,20-methano-7-thia-1,6-(p-phenylene)-2,3,4,5tetranorprost-8,13-dienoic Acid Methyl Ester

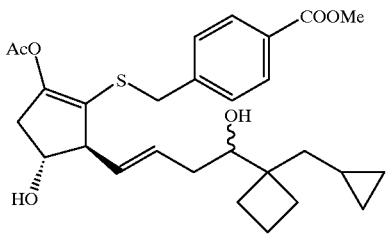

Less Polar

TLC Rf 0.38 (ethyl acetate:hexane=1:1);

NMR (CDCl₃): δ 7.97 (2H, d, J=8.0 Hz), 7.37 (2H, d, J=8.0 Hz), 5.57 (1H, ddd, J=15.0, 8.5, 6.0 Hz), 5.26 (1H, dd, J=15.0, 9.0 Hz), 4.20–4.15 (1H, m), 3.90 (3H, s), 3.86 (2H, s), 3.64 (1H, dd, J=10.0, 2.0 Hz), 3.06 (1H, dd, J=8.5, 3.0 Hz), 2.92 (1H, ddd, J=16.5, 7.0, 1.5 Hz), 2.49 (1H, ddd, J=16.5, 4.0, 1.5 Hz), 2.35–2.20 (1H, m), 2.15 (3H, s), 2.10–1.50 (8H, m), 1.55 (1H, dd, J=14.0, 6.5 Hz), 1.33 (1H, dd, J=14.0, 6.0 Hz), 0.90–0.70 (1H, m), 0.55–0.45 (1H, m), 0.15–0.05 (1H, m).

More Polar

TLC: Rf 0.32 (ethyl acetate: hexane=1:1);

NMR (CDCl₃): δ 7.97 (2H, d, J=8.0 Hz), 7.36 (2H, d, J=8.0 Hz), 5.70–5.50 (1H, m), 5.35 (1H, dd, J=15.5, 8.5 Hz), 4.20–4.05 (1H, 5 m), 3.91 (3H, s), 3.88 (2H, s), 3.67 (1H, dd, J=9.5, 2.0 Hz), 3.15–3.05 (1H, m), 2.92 (1H, dd, J=16.0, 6.5 Hz), 2.55–1.60 (7H, m), 1.51 (1H, dd, J=14.5, 7.0 Hz), 1.35 (1H, dd, J=14.5, 6.0 Hz), 0.90–0.70 (1H, m), 0.60–0.45 (2H, m), 0.15–0.05 (2H, m).

Example 4

(11α,13E) -9-Oxo-11,16-dihydroxy-17,17-propano-7-thia-1,6-(p-phenylene)-2,3,4,5,20-pentanorprost-13-enoic Acid Methyl Ester

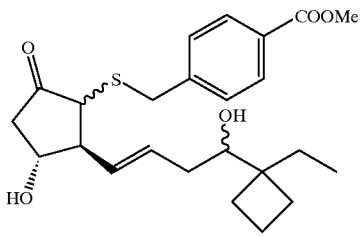

To a solution of the compound prepared in example 3 (112 mg, more polar) in DMSO/phosphoric acid buffer (3 ml+3 ml) stirred at room temperature, was added lipase (200 mg, Amano-PS), and the mixture was stirred at room temperature for 2 hours. The reaction was quenched by addition of a saturated solution of sodium sulfate. The mixture was extracted with ethyl acetate three times. The organic layer was washed with water twice, with brine once. The extract was dried over anhydrous magnesium sulfate and concentrated. The residue was purified by column chromatography on silica gel (Merck Kiesel gel 7734, 20 ml, ethyl acetate/hexane=1/1→2/1) to give the title compound (77 mg) having the following physical data as a light yellow oil.

More Polar

TLC: Rf 0.36, 0.40 (ethyl acetate:hexane=3:2); NMR (CDCl₃): δ 7.97 (2H, d, J=8.0 Hz), 7.44, 7.42 (2H, each-d, J=8.0 Hz), 5.80–5.16 (2H, m), 4.50–3.70 (4H, m), 3.91 (3H, s), 3.52 (1H, dd, J=10.0, 2.0 Hz), 3.24–2.64 (3H, m), 2.50–1.20 (12H, m), 0.91 (3H, t, J=7.0 Hz).

By the same procedure as described above, using the compound prepared in example 3 (less polar), the compound having the following physical data was obtained.

Less Polar

TLC: Rf 0.40 (ethyl acetate:hexane=3:2);

NMR (CDCl₃): δ 7.98 (2H, d, J=8.0 Hz), 7.44, 7.43 (2H, each-d, J=8.0 Hz), 5.75–5.22 (2H, m), 4.52–3.70 (3H, m), 3.91 (3H, s), 3.51 (1H, dd, J=9.0, 2.5 Hz), 3.30–2.68 (3H, m), 2.50–2.10 (3H, m), 2.10–1.30 (10H, m), 0.92 (3H, t, J=7.5 Hz).

Example 4(a)–4(d)

By the same procedure as example 4, using the compounds prepared in example 3(a)–3(d), the compounds having the following physical data were obtained.

Example 4(a)

(11α,13E) -9-Oxo-11,16-dihydroxy-17,17-propano-7-thia-1,6-(p-phenylene)-2,3,4,5-tetranorprost-13-enoic Acid Methyl Ester

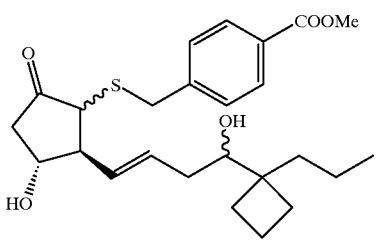

Less Polar

TLC: Rf 0.49 (ethyl acetate:hexane=3:2);

NMR (CDCl₃): δ 7.98 (2H, d, J=8.0 Hz), 7.42 (2H, d, J=8.0 Hz), 5.75–5.23 (2H, m), 4.50–3.70 (3H, m), 3.91 (3H, s), 3.50 (1H, dd, J=10.0, 2.0 Hz), 3.30–2.55 (3H, m), 2.55–2.10 (3H, m), 2.10–1.20 (12H, m), 0.94 (3H, t, J=6.0 Hz). more polar TLC: Rf 0.42, 0.49 (ethyl acetate:hexane=3:2);

NMR (CDCl₃): δ 7.97 (2H, d, J=8.0 Hz), 7.43, 7.42 (2H, each-d, J=8.0 Hz), 5.75–5.18 (2H, m), 4.50–3.62 (3H, m), 3.90 (3H, s), 3.52 (1H, dd, J=10.0, 2.0 Hz), 3.22–2.65 (3H, m), 2.55–1.20 (15H, m), 0.94 (3H, t, J=6.5 Hz).

Example 4(b)

(11α,13E)-9-Oxo-11,16-dihydroxy-17,17-propano-7-thia-1,6-(p-phenylene)-2,3,4,5-tetranorprost-13,19-dienoic Acid Methyl Ester

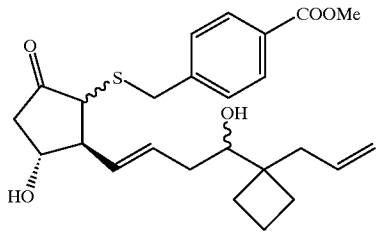

Less Polar

TLC: Rf 0.40 (ethyl acetate:hexane=3:2);

NMR (CDCl$_3$): δ 7.98 (2H, d, J=8.0 Hz), 7.43, 7.42 (2H, each-d, J=8.0 Hz), 6.16–5.80 (1H, m), 5.75–5.22 (2H, m), 5.18–5.02 (2H, m), 4.50–3.70 (3H, m), 3.91 (3H, s), 3.51 (1H, dd, J=9.5, 2.0 Hz), 3.30–2.67 (2H, m), 2.60–1.50 (13H, m).

More Polar

TLC: Rf 0.36, 0.40 (ethyl acetate:hexane=3:2); NMR (CDCl$_3$): δ 7.97 (2H, d, J=8.0 Hz), 7.43, 7.41 (2H, each-d, J=8.0 Hz), 6.50–5.80 (1H, m), 5.70–5.20 (2H, m), 5.20–5.00 (2H, m), 4.50–3.68 (4H, m), 3.91 (3H, s), 3.51 (1H, d, J=10.0 Hz), 3.22–2.65 (2H, m), 2.50–1.60 (12H, m).

Example 4(c)

(11α,13E)-9-Oxo-11,16-dihydroxy-19-methyl-17,17-propano-7-thia-1,6-(p-phenylene)-2,3,4,5-tetranorprost-13-enoic Acid Methyl Ester

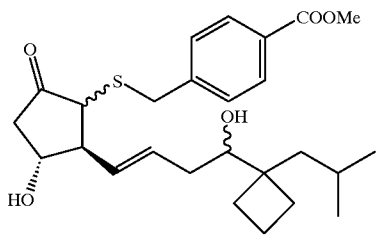

Less Polar

TLC Rt 0.60 (ethyl acetate:hexane=3:2);

NMR (CDCl$_3$): δ 7.99 (2H, d, J=8.0 Hz), 7.44, 7.43 (2H, each-d, J=8.0 Hz), 5.80–5.25 (2H, m), 4.55–3.70 (3H, m), 3.91 (3H, s), 3.64–3.52 (1H, m), 3.30–2.70 (2H, m), 2.60–1.40 (14H, m), 1.40–1.20 (1H, m), 0.93, 0.92 (6H, each-d, J=6.5 Hz).

More Polar

TLC: Rf 0.52, 0.58 (ethyl acetate:hexane=3:2);

NMR (CDCl$_3$): δ 7.98 (2H, d, J=8.0 Hz), 7.44, 7.43 (2H, each-d, J=8.0 Hz), 5.80–5.20 (2H, m), 4.55–3.70 (3H, m), 3.91 (3H, s), 3.62 (1H, d, J=10.0 Hz), 3.24–2.68 (3H, m), 2.55–2.20 (3H, m), 2.20–1.60 (10H, m), 1.54 (1H, dd, J=14.0, 6.5 Hz), 1.32 (1H, dd, J=14.0, 5.5 Hz), 0.91, 0.90 (6H, each-d, J=6.5 Hz).

Example 4(d)

(11α,13E) -9-Oxo-11,16-dihydroxy-17,17-propano-19,20-methano-7-thia-1,6-(p-phenylene)-2,3,4,5-tetranorprost-13-enoic Acid Methyl Ester

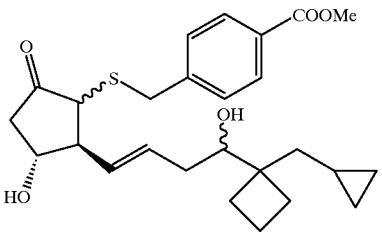

Less Polar

TLC Rf 0.54 (ethyl acetate:hexane=3:2);

NMR (CDCl3): δ 7.98 (2H, d, J=8.0 Hz), 7.44, 7.43 (2H, each-d, J=8.0 Hz), 5.80–5.24 (2H, m), 4.55–3.70 (3H, m), 3.91 (3H, s), 3.70–3.60 (1H, m), 3.30–2.70 (2H, m), 2.60–2.15 (4H, m), 2.10–1.60 (8H, m), 1.52 (1H, dd, J=14.0, 6.5 Hz), 1.34 (1H, dd, J=14.0, 6.0 Hz), 1.00–0.65 (1H, m), 0.60–0.45 (2H, m), 0.16–0.05 (2H, m).

More Polar

TLC: Rf 0.43, 0.49 (ethyl acetate:hexane=3:2);

NMR (CDCl$_3$): δ 7.98 (2H, d, J=8.0 Hz), 7.44, 7.42 (2H, each-d, J=8.0 Hz), 5.80–5.16 (2H, m), 4.50–3.76 (3H, m), 3.91 (3H, s), 3.66 (1H, dd, J=10.5, 2.0 Hz), 3.22–2.66 (3H, m), 2.55–2.20 (3H, m), 2.10–1.60 (8H, m), 1.60–1.30 (2H, m), 0.85–0.68 (1H, m), 0.58–0.45 (2H, m), 0.18–0.04 (2H, m).

Example 5

(11α,13E)-9-Oxo-11,16-dihydroxy-17,17-propano-7-thia-1,6-(p-phenylene)-2,3,4,5,20-pentanorprost-13-enoic Acid

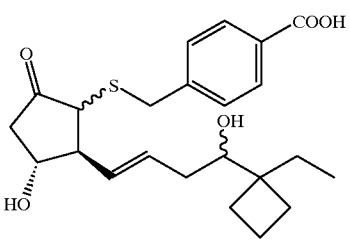

By the same procedure as example 2, using the compound prepared in example 4 (more polar), the compound having the following physical data was obtained.

More Polar

TLC: Rf 0.32, 0.37 (ethyl acetate:hexane:acetic acid 6:4:0.1);

NMR (CDCl$_3$): δ 8.03 (2H, d, J=8.5 Hz), 7.45 (2H, d, J=8.5 Hz), 5.70–5.20 (2H, m), 4.54–3.70 (3H, m), 3.56 (1H, dd, J=9.5, 2.0 Hz), 3.25–1.30 (16H, m), 0.92 (3H, t, J=7.5 Hz).

Example 5(a)–5(d)

By the same procedure as example 2, using the compounds prepared in example 4(a)–4(d), the compounds having the following physical data were obtained.

Example 5(a)

(11α,13E)-9-Oxo-11,16-dihydroxy-17,17-propano-7-thia-1,6-(p-phenylene)-2,3,4,5-tetranorprost-13-enoic Acid

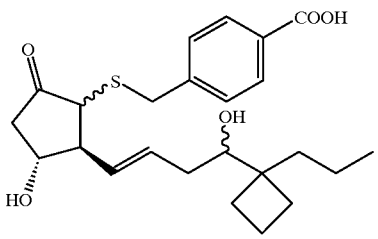

Less Polar

TLC Rf 0.34 (ethyl acetate:hexane:acetic acid= 200:100:1);

NMR (CDCl$_3$): δ 8.02 (2H, d, J=8.0 Hz), 7.45 (2H, d, J=8.0 Hz), 5.80–5.25 (2H, m), 4.55–3.66 (4H, m), 4.25 (3H, brs), 3.53 (1H, dd, J=10.0, 2.5 Hz), 3.30–2.10 (5H, m), 2.10–1.20 (10H, m), 0.93 (3H, t, J=7.0 Hz).

More Polar

TLC: Rf 0.29, 0.34 (ethyl acetate:hexane:acetic acid=200 100:1);

NMR (CDCl$_3$): δ 8.02 (2H, d, J=8.0 Hz), 7.44 (2H, d, J=8.0 Hz), 5.80–5.20 (2H, m), 4.55–3.70 (4H, m), 3.55 (1H, dd, J=10.0, 2.0 Hz), 3.40–2.65 (2H, m), 3.20 (3H, brs), 2.60–2.20 (3H, m), 2.10–1.20 (10H, m), 0.94 (3H, t, J=6.5 Hz).

Example 5(b)

(11α,13E)-9-Oxo-11,16-dihydroxy-17,17-propano-7-thia-1,6-(p-phenylene)-2,3,4,5-tetranorprost-13,19-dienoic Acid

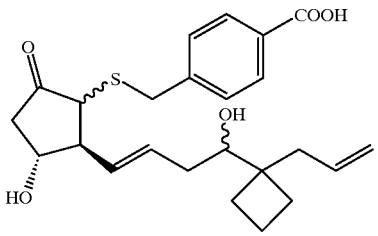

More Polar

TLC: Rf 0.33, 0.39 (ethyl acetate:hexane:acetic acid= 6:4:0.1);

NMR (CDCl$_3$): δ 8.03 (2H, d, J=8.0 Hz), 7.46 (2H, d, J=8.0 Hz), 6.05–5.80 (1H, m), 5.70–5.50 (1H, m), 5.36–5.20 (1H, m), 5.20–5.04 (2H, m), 4.20–3.70 (3H, m), 3.54 (1H, dd, J=10.0, 3.0 Hz), 2.85–2.60 (2H, m), 2.60–1.60 (14H, m).

Example 5(c)

(11α,13E)-9-Oxo-11,16-dihydroxy-19-methyl-17,17-propano-7-thia-1,6-(p-phenylene)-2,3,4,5-tetranorprost-13-enoic Acid

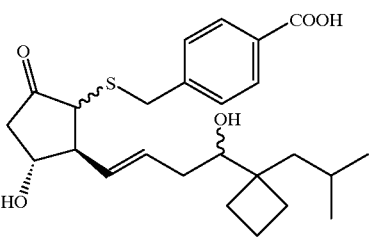

More Polar

TLC: Rf 0.32, 0.37 (ethyl acetate hexane:acetic acid= 6:3:0.1);

NMR (CDCl$_3$): δ 8.02 (2H, d, J=8.0 Hz), 7.46, 7.45 (2H, each-d, J=8.0 Hz), 5.80–5.20 (2H, m), 4.52–3.95 (2H, m), 3.95–3.60 (2H, m), 3.30–2.70 (3H, m), 2.65–2.20 (3H, m), 2.15–1.60 (9H, m), 1.54 (1H, dd, J=14.0, 7.0 Hz), 1.33 (1H, dd, J=14, 6.5 Hz), 0.91 (6H, d, J=6.5 Hz).

Example 5(d)

(11α,13E) -9-Oxo-11,16-dihydroxy-17,17-propano-19,20-methano-7-thia-1,6-(p-phenylene)-2,3,4,5-tetranorprost-13-enoic Acid

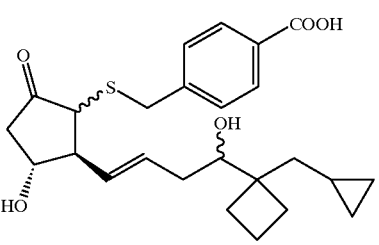

More Polar

TLC: Rf 0.25, 0.31 (ethyl acetate:hexane:acetic acid= 6:3:0.1);

NMR (CDCl$_3$): δ 8.02 (2H, d, J=8.0 Hz), 7.46, 7.45 (2H, each-d, J=8.0 Hz), 5.70–5.16 (2H, m), 4.52–3.62 (5H, m), 3.30–2.70 (3H, m), 2.65–2.20 (3H, m), 2.10–1.60 (7H, m), 1.50 (1H, dd, J=14.0, 6.5 Hz), 1.38 (1H, dd, J=14, 6.0 Hz), 0.85–0.70 (1H, m), 0.58–0.45 (2H, m), 0.16–0.05 (2H, m).

Reference Example 7

(11α,13E) -9-Oxo-11,16-bis (t-butyldimethylsilyloxy) -17,17-propano-6-thia-1,6-(p-phenylene)-2,3,4,5-tetranorprost-13-enoic Acid Methyl Ester

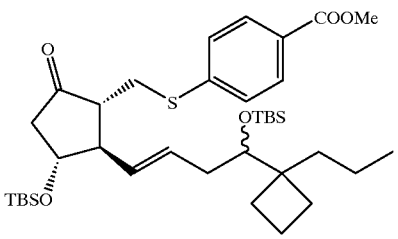

Under atmosphere of argon, to a solution of the compound prepared in reference example 3 (102 mg) in methanol (2 ml), were added 4-mercapto methyl benzoate (32 mg) and piperidine (10 μl) at −78° C. The mixture was stirred at −78° C. for 1 hour. To this solution, a saturated aqueous solution of ammonium chloride was added. The mixture was extracted with ethyl acetate. The organic layer was washed, dried, and then concentrated. The residue was purified by column chromatography on silica gel to give the title compound (77 mg) having the following physical data.

TLC: Rf 0.58 (hexane:ethyl acetate=4:1).

Example 6

(11α,13E)-9-Oxo-11,16-dihydroxy-17,17-propano-6-thia-1,6(p-phenylene)-2,3,4,5-tetranorprost-13-enoic acid methyl ester

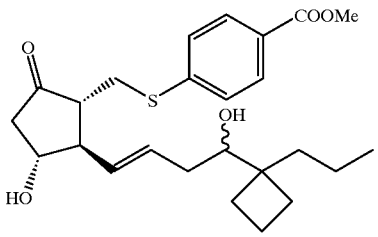

To a solution of the compound prepared in reference example 7 (76 mg) in acetonitrile (20 ml), was added an aqueous solution of hydrofluoric acid (1 ml; 47%) under cooling with ice, and the mixture was stirred at room temperature for 1.5 hours. To this solution, was added a saturated aqueous solution of sodium bicarbonate. The mixture was vigorously stirred, and extracted with ethyl acetate. The organic layer was washed with a saturated aqueous solution of sodium bicarbonate, with brine, and dried, and then concentrated in vacuo. The residue was purified by Lobar column (Lobar column size A, hexane/ethyl acetate=2/3) to give the title compounds (less polar: 18 mg, more polar: 16 mg) having the following physical data.

Less Polar

TLC: Rf 0.42 (hexane:ethyl acetate=2:3);

NMR (CDCl$_3$): δ 7.94 (2H, d, J=8.4 Hz), 7.35 (2H, d, J=8.4 Hz), 5.64 (1H, ddd, J=15.0, 8.2, 5.6 Hz), 5.47 (1H, dd, J=15.0, 8.2 Hz), 4.20–4.05 (1H, m), 3.90 (3H, s), 3.54 (1H, dd, J=10.0, 2.2 Hz), 3.43 (1H, dd, J=13.3, 4.1 Hz), 3.14 (1H, dd, J=13.3, 6.7 Hz), 2.81 (1H, ddd, J=18.6, 7.8, 1.0 Hz), 2.61 (1H, dt, J=11.6, 8.2 Hz), 2.45–2.20 (2H, m), 2.29 (1H, dd, J=18.6, 9.2 Hz), 2.10–1.20 (13H, m), 0.95 (3H, t, J=6.7 Hz).

More Polar

TLC: Rf 0.34 (hexane:ethyl acetate=2:3);

NMR (CDCl$_3$): δ 7.93 (2H, d, J=8.6 Hz), 7.33 (2H, d, J=8.6 Hz), 5.62 (1H, ddd, J=15.2, 7.8, 5.4 Hz), 5.42 (1H, dd, J=15.2, 8.2 Hz), 4.15–4.00 (1H, m), 3.90 (3H, s), 3.54 (1H, dd, J=9.8, 2.6 Hz), 3.35 (1H, dd, J=13.4, 4.6 Hz), 3.19 (1H, dd, J=13.4, 5.7 Hz), 2.79 (1H, ddd, J=18.8, 7.6, 1.0 Hz), 2.60 (1H, dt, J=12.2, 8.2 Hz), 2.45–2.20 (2H, m), 2.28 (1H, dd, J=18.8, 9.4 Hz), 2.10–1.20 (13H, m), 0.95 (3H, t, J=6.8 Hz).

Example 7

(11α,13E)-9-Oxo-11,16-dihydroxy-17,17-propano-6-thia-1,6-(p-phenylene)-2,3,4,5-tetranorprost-13-enoic Acid

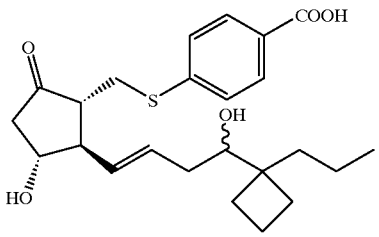

By the same procedure as example 2, using the compounds prepared in example 6, the title compounds having the following physical data were obtained.

Less Polar

TLC: Rf 0.33 (hexane:ethyl acetate:acetic acid=2:3:0.05);
NMR (CDCl$_3$): δ 7.96 (2H, d, J=8.4 Hz), 7.35 (2H, d, J=8.4 Hz), 5.66 (1H, ddd, J=15.4, 7.8, 5.4 Hz), 5.49 (1H, dd, J=15.4, 7.8 Hz), 4.20–4.05 (1H, m), 4.00–2.50 (3H, br), 3.57 (1H, dd, J=10.0, 2.2 Hz), 3.43 (1H, dd, J=13.4, 4.0 Hz), 3.16 (1H, dd, J=13.4, 6.4 Hz), 2.82 (1H, ddd, J=18.8, 7.2, 1.0 Hz), 2.62 (1H, dt, J=12.0, 8.4 Hz), 2.50–2.20 (2H, m), 2.30 (1H, dd, J=18.8, 9.2 Hz), 2.15–1.20 (13H, m), 0.94 (3H, t, J=6.7 Hz).

More Polar

TLC: Rf 0.27 (hexane ethyl acetate:acetic acid=2:3:0.05);
NMR (CDCl3): δ 7.96 (2H, d, J=8.4 Hz), 7.34 (2H, d, J=8.4 Hz), 5.70–5.35 (2H, m), 4.20–4.00 (1H, m), 4.00–2.50 (3H, br), 3.58 (1H, d, J=10.0 Hz), 3.35 (1H, dd, J=13.8, 4.4 Hz), 3.20 (1H, dd, J=13.8, 5.6 Hz), 2.80 (1H, dd, J=18.8, 7.2 Hz), 2.73–2.55 (1H, m), 2.50–2.15 (3H, m), 2.15–1.20 (11H, m), 0.94 (3H, t, J=6.9 Hz).

Reference Example 8

(9α,11α,13E)-9-Hydroxy-11,16-bis(t-butyldimethylsilyloxy)-17,17-propano-19,20-methano-1,6-(p-phenylene)-2,3,4,5-tetranorprost-13-enoic Acid Methyl Ester

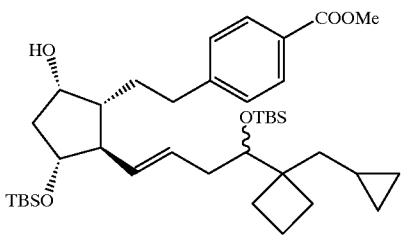

Under atmosphere of argon, to a solution of (11α,13E)-9-oxo-11,16-bis(t-butyldimethylsilyloxy)-17,17-propano-19,20-methano-1,6-(p-phenylene)-2,3,4,5-tetranorprost-13-enoic acid methyl ester (170 mg, an intermediate in example 1(b); which was prepared by the same procedure as provided in reference example 1,2,3 and 4) in anhydrous THF (2.5 ml), was added lithium tri-s-butyl borohydride (1.0 M, 279 μl) was added dropwise at −78° C., and the mixture was stirred at −78° C. for 1.5 hours. To the mixture, was added dropwise an aqueous solution of hydrogen peroxide (0.5 ml), and the mixture was warmed to 0° C. The mixture was acidified by addition of 1N hydrochloric acid, and the mixture was extracted with ethyl acetate. The organic layer was washed, dried, concentrated in vacuo. The residue was purified by column chromatography on silica gel (Merck

Reference Example 9

(9α,11α,13E)-9-Acetyloxy-11,16-dihydroxy-17,17-propano-19,20-methano-1,6-(p-phenylene)-2,3,4,5-tetranorprost-13-enoic Acid Methyl Ester

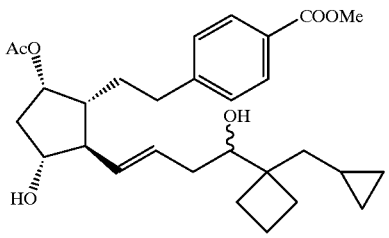

To a solution of the compound prepared in reference example 8 (80 mg) and dimethylaminopyridine (5 mg) in pyridine (2 ml), was added dropwise acetic anhydride (112 ml), and the mixture was stirred at room temperature for 2.5 hours. The reaction mixture was poured into ice-water. The mixture was extracted with ethyl ether. The organic layer was washed, dried, concentrated in vacuo, to give a crude product. To a solution of the crude product in acetonitrile (7 ml), was added dropwise an aqueous solution of hydrofluoric acid (0.35 ml, 47%), and the mixture was stirred at room temperature for 1.5 hours. The reaction mixture was poured into cooled ethyl acetate/a saturated aqueous solution of sodium bicarbonate. The mixture was extracted with ethyl acetate. The organic layer was washed, dried, and concentrated in vacuo. The residue was purified by column chromatography on silica gel (Lobar size A, hexane/ethyl acetate=3/2→1/1) to give the title compounds (less polar: 25 mg, more polar: 24 mg) having the following physical data.

less polar

TLC: Rf 0.46 (hexane:ethyl acetate=2:3);

NMR (CDCl$_3$): δ 7.94 (2H, d, J=8.3 Hz), 7.20 (2H, d, J=8.3 Hz), 5.66 (1H, m), 5.32 (1H, dd, J=14, 8.8 Hz), 5.22 (1H, m), 3.90 (3H, s), 3.87 (1H, m), 3.68 (1H, dd, J=9.8, 1.9 Hz), 2.79–1.43 (17H, m), 2.09 (3H, s), 1.34 (1H, dd, J=14, 6.2 Hz), 0.78 (1H, m), 0.49 (2H, m), 0.10 (2H, m).

More Polar

TLC: Rf 0.39 (hexane:ethyl acetate=2:3);

NMR (CDCl$_3$): δ 7.94 (2H, d, J=8.4 Hz), 7.20 (2H, d, J=8.4 Hz), 5.61 (1H, ddd, J=15, 8.9, 5.9 Hz), 5.25 (2H, m), 3.90 (3H, s), 3.82 (1H, m), 3.66 (1H, dd, J=10, 2.4 Hz), 2.80–1.42 (17H, m), 2.09 (3H, s), 1.34 (1H, dd, J=14, 5.9 Hz), 0.77 (1H, m), 0.49 (2H, m), 0.10 (2H, m).

Reference Example 10

(9α,11α,13E)-9-Hydroxy-11,16-bis(t-butyldimethylsilyloxy)-17,17-propano-19,20-methano-1,6-(p-phenylene)-2,3,4,5-tetranorprost-13-enoic Acid Methyl Ester

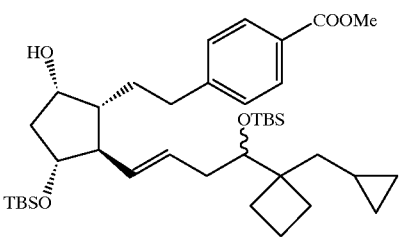

Under atmosphere of argon, to a solution of the compound prepared in reference example 9 (22 mg, more polar) in anhydrous methylene chloride (0.5 ml) were added dropwise, 2,6-lutidine (16 μl) and trifluoromethanesulfonic acid t-butyldimethylsilyl ester (25 μl), and the mixture was stirred at room temperature for 2 hours. To the reaction mixture, water was added. The mixture was extracted with ethyl acetate. The organic layer was washed, dried, and concentrated in vacuo to give a crude compound.

To a solution of the crude compound in anhydrous methanol (1 ml), potassium carbonate (8 mg) was added, and the mixture was stirred for 15 hours. The mixture was acidified by addition of 1N hydrochloric acid at 0° C., and the mixture was extracted with ethyl acetate. The organic layer was washed, dried, and concentrated in vacuo. The residue was purified by column chromatography on silica gel (Merck 7734, 2 g, hexane/ethyl acetate=25/1→15/1) to give the title compound (28 mg) having the following physical data.

TLC: Rf 0.33 (hexane:ethyl acetate=9:1);

NMR (CDCl$_3$): 7.94 (2H, d, J=8.2 Hz), 7.26 (2H, d, J=8.2 Hz), 5.45 (1H, dt, J=15, 7.4 Hz), 5.17 (1H, dd, J=15, 8.6 Hz), 4.17 (1H, m), 3.99 (1H, m), 3.89 (3H, s), 3.64 (1H, t, J=7.3 Hz), 2.96–2.52 (3H, m), 2.29–1.41 (14H, m), 1.21 (1H, dd, J=14, 6.7 Hz), 0.88 (19H, m), 0.47 (2H, m), 0.05 (14H, m).

Reference Example 11

(9α,11α,13E)-9-Tosyloxy-11,16-bis(t-butyldimethylsilyloxy)-17,17-propano-19,20-methano-1,6-(p-phenylene)-2,3,4,5-tetranorprost-13-enoic Acid Methyl Ester

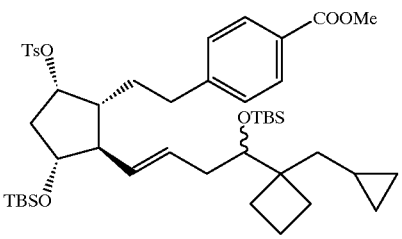

Under atmosphere of argon, to a solution of the compound prepared in reference example 10 (28 mg) in anhydrous pyridine (1.5 ml), was added tosyl chloride (80 mg) at 0° C. The mixture was stirred at room temperature overnight. To the reaction solution was added water (0.5 ml), and the mixture was stirred for 5 minutes. The mixture was extracted with ethyl acetate. The organic layer was washed, dried, concentrated in vacuo to give the title compound (34 mg) having the following physical data.

TLC: Rf 0.82 (toluene:isopropylalcohol=30:1).

Reference Example 12

(9β,11α,13E) -9-Chloro-11,16-bis(t-butyldimethylsilyloxy)-17,17-propano-19,20-methano-1,6-(p-phenylene)-2,3,4,5-tetranorprost-13-enoic Acid Methyl Ester

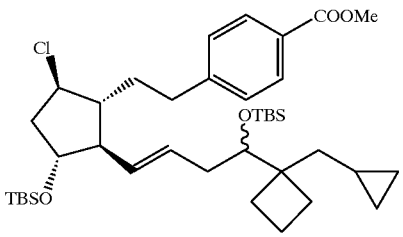

Under atmosphere of argon, to a solution of the compound prepared in reference example 11 (34 mg) in anhydrous toluene (2 ml), tetrabutylammonium chloride (116 mg) was added quickly, and the mixture was stirred at 55° C. for 1 hour. The reaction mixture was diluted with ethyl acetate, washed, dried and concentrated in vacuo to give the title compound having the following physical data.

TLC: Rf 0.88 (toluene:isopropylalcohol=30:1).

Example 8

(9β,11α,13E)-9-Chloro-11,16-dihydroxy-17,17-propano-19,20-methano-1,6-(p-phenylene)-2,3,4,5-tetranorprost-13-enoic Acid Methyl Ester

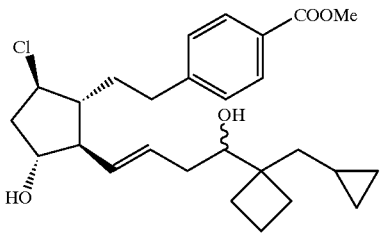

By the same procedure as example 1, using the compound prepared in reference example 12, the title compound having the following physical data was obtained.

More Polar

TLC: Rf 0.58 (hexane:ethyl acetate=1:1);

NMR (CDCl$_3$): δ 7.94 (2H, d, J=8.3 Hz), 7.26 (2H, d, J=8.3 Hz), 5.59 (1H, ddd, J=15, 8.6, 5.4 Hz), 5.38 (1H, dd, J=15, 8.0 Hz), 4.09 (2H, m), 3.90 (3H, s), 3.66 (1H, dd, J=10, 2.0 Hz), 3.08 (1H, bs), 2.78 (2H, t, J=7.8 Hz), 2.40–1.62 (14H, m), 1.50 (1H, dd, J=14, 6.6 Hz), 1.36 (1H, dd, J=14, 6.3 Hz), 0.77 (1H, m), 0.50 (2H, m), 0.10 (2H, m).

Example 8(a)–8(c)

By the same procedure as reference example 8, 9, 10, 11, 12 and example 1, the compounds having the following physical data were obtained.

Example 8(a)

(9β,11α,13E)-9-Chloro-11,16-dihydroxy-17,17-propano-19-methyl-1,6-(p-phenylene)-2,3,4,5-tetranorprost-13-enoic Acid Methyl Ester

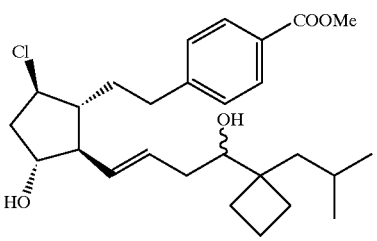

More Polar

TLC Rf 0.65 (hexane:ethyl acetate=1:1);

NMR (CDCl$_3$): δ 7.95 (2H, d, J=8.5 Hz), 7.26 (2H, d, J=8.5 Hz), 5.60 (1H, ddd, J=15, 8.6, 5.2 Hz), 5.40 (1H, dd, J=15, 7.7 Hz), 4.09 (2H, m), 3.90 (3H, s), 3.61 (1H, dd, J=10, 1.8 Hz), 2.86 (1H, bs), 2.78 (2H, t, J=7.8 Hz), 2.38–1.62 (15H, m), 1.54 (1H, dd, J=14, 6.8 Hz), 1.33 (1H, dd, J=14, 6.5 Hz), 0.92 (3H, d, J=6.2 Hz), 0.91 (3H, d, J=6.1 Hz).

Example 8(b)

(9β,11α,13E)-9-Chloro-11,16-dihydroxy-17,17-propano-1,6-(p-phenylene)-2,3,4,5,20-pentanorprost-13-enoic Acid Methyl Ester

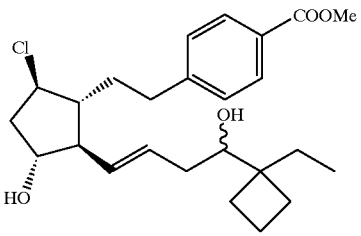

More Polar

TLC: Rf 0.45 (toluene:isopropylalcohol=9:1);

NMR (CDCl$_3$): δ 7.95 (2H, d, J=8.0 Hz), 7.25 (2H, d, J=8.0 Hz), 5.58 (1H, ddd, J=15.4, 8.0, 5.6 Hz), 5.38 (1H, dd, J=15.4, 8.0 Hz), 4.16–4.02 (2H, m), 3.90 (3H, s), 3.53 (1H, dd, J=10.0, 2.2 Hz), 2.78 (2H, t, J=7.8 Hz), 2.37–1.32 (18H, m), 0.91 (3H, t, J=7.4 Hz).

Example 8(c)

(9β,11α,13E)-9-Chloro-11,16-dihydroxy-17,17-propano-1,6-(p-phenylene)-2,3,4,5-tetranorprost-13,19-dienoic Acid Methyl Ester

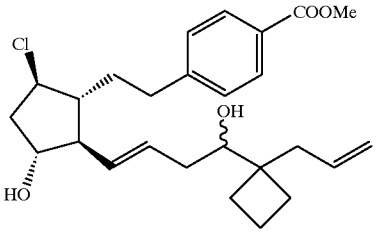

More Polar

TLC Rf 0.39 (toluene:isopropylalcohol=9:1);

NMR (CDCl$_3$): δ 7.95 (2H, d, J=8.4 Hz), 7.25 (2H, d, J=8.4 Hz), 5.93 (1H, ddt, J=17.2, 9.8, 7.4 Hz), 5.56 (1H, ddd, J=15.4, 8.0, 5.6 Hz), 5.37 (1H, dd, J=15.4, 8.0 Hz), 5.15–5.06 (2H, m), 4.15–4.02 (2H, m), 3.90 (3H, s), 3.52 (1H, dd, J=10.2, 2.6 Hz), 2.77 (2H, t, J=7.6 Hz), 2.42–1.60 (18H, m).

Example 9

(9β,11α,13E) -9-Chloro-11,16-dihydroxy-17,17-propano-19,20-methano-1,6-(p-phenylene)-2,3,4,5-tetranorprost-13-enoic Acid

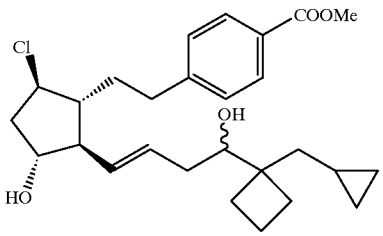

To a solution of the compound prepared in example 8 (10 mg) in methanol (1 ml), was added 2N aqueous solution of sodium hydroxide (0.5 ml) and the mixture was stirred at room temperature for 4 hours. The mixture was acidified by addition of 1N hydrochloric acid and the mixture was extracted with ethyl acetate. The organic layer was washed, dried, concentrated in vacuo. The residue was purified by column chromatography on silica gel (Wakogel C-200, 1 g, hexane/ethyl acetate=2/1→1/1) to give the title compound (9.3 mg) having the following physical data TLC: Rf 0.26 (hexane:ethyl acetate=1:2);

NMR (CDCl₃): δ 8.01 (2H, d, J=8.0 Hz), 7.28 (2H, d, J=8.0 Hz), 5.57 (1H, m), 5.39 (1H, m), 4.38 (3H, br), 4.10 (2H, m), 3.70 (1H, bd, J=8.4 Hz), 2.79 (2H, t, J=7.6 Hz), 2.40–1.62 (14H, m), 1.52 (1H, dd, J=14, 6.6 Hz), 1.36 (1H, dd, J=14, 6.4 Hz), 0.78 (1H, m), 0.49 (2H, m), 0.10 (2H, m).

Example 9(a)–Example 9(c)

By the same procedure as example 9, using the compounds prepared in example 8(a)–8(c), the compounds having the following physical data were obtained.

Example 9(a)

(9β,11α,13E)-9-Chloro-11,16-dihydroxy-17,17-propano-19-methyl-1,6-(p-phenylene)-2,3,4,5-tetranorprost-13-enoic acid

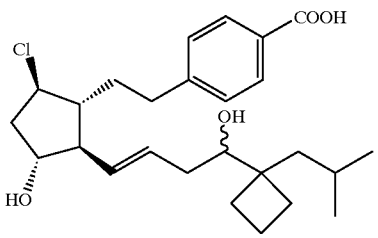

TLC Rf 0.33 (hexane ethyl acetate=1:2);

NMR (CDCl): δ 8.00 (2H, d, J=8.2 Hz), 7.27 (2H., d, J=8.2 Hz), 5.60 (1H, ddd, J=15, 8.8, 5.2 Hz), 5.42 (1H, dd, J=15, 7.8 Hz), 4.12 (2H, m), 3.69 (3H, br), 3.63 (1H, dd, J=10, 1.8 Hz), 2.79 (2H, t, J=7.9 Hz), 2.38–1.62 (15H, m), 1.54 (1H, dd, J=14, 6.8 Hz), 1.33 (1H, dd, J=14, 6.4 Hz), 0.91 (3H, d, J=6.6 Hz, 0.90 (3H, d, J=6.2 Hz).

Example 9(b)

(9β,11α,13E)-9-Chloro-11,16-dihydroxy-17,17-propano-1,6-(p-phenylene)-2,3,4,5,20-pentanorprost-13-enoic acid

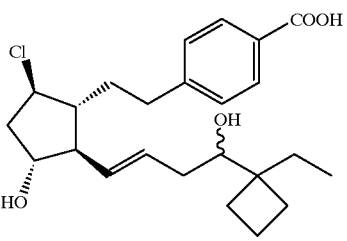

TLC: Rf 0.14 (hexane:ethyl acetate=1:1);

NMR (CDCl₃): δ 8.00 (2H, d, J=8.0 Hz), 7.27 (2H, cl, J=18.0 Hz), 5.58 (1H, ddd, J=15.4, 8.4, 6.6 Hz), 5.40 (1H, dd, J=15.4, 8.2 Hz), 4.40–3.00 (3H, br), 4.18–4.03 (2H, m), 3.56 (1H, dd, J=10.2, 2.2 Hz), 2.79 (2H, t, J=7.6 Hz), 2.38–1.30 (16H, m), 0.91 (3H, t, J=7.8 Hz).

Example 9(c)

(9β,11α,13E) -9-Chloro-11,16-dihydroxy-17,17-propano-1,6-(p-phenylene)-2,3,4,5-tetranorprost-13,19-dienoic acid

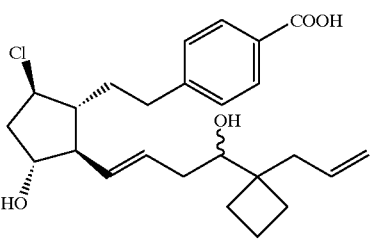

TLC: Rf 0.15 (hexane:ethyl acetate=1:1);

NMR (CDCl₃): δ 8.00 (2H, d, J=8.0 Hz), 7.27 (2H, d, J=18.0 Hz), 5.93 (1H, ddt, J=17.4, 10.0, 7.2 Hz), 5.65–5.50 (1H, m), 5.38 (1H, dd, J=15.4, 8.4 Hz), 5.15–5.06 (2H, m), 4.80–3.60 (3H, br), 4.18–4.00 (2H, m), 3.55 (1H, bd, J=8.4 Hz), 2.78 (2H, t, J=7.6 Hz), 2.41–1.60 (16H, m).

Formulation Example 1

The following compounds were admixed in the conventional method, dried, and was added microcrystalline cellulose thereon to weigh 10 g in total, mixed until homogeneous and punched out in conventional method to obtain 100 tablets each containing 30 μg of active ingredient.

The solution of (11α,13E)-9-oxo-11,16-dihydroxy-17,17-propano-1,6-(p-phenylene)-2,3,4,5-tetranorprost-13-enoic

| | |
|---|---|
| acid (3 mg) in ethanol | 10 ml |
| Magnesium stearate | 100 mg |
| silicon dioxide | 20 mg |
| talc | 10 mg |
| Carboxymethylcellulose calcium | 200 mg |
| Microcrystalline cellulose | 5.0 g |

What is claimed is:

1. An ω-cycloalkyl-prostaglandin $E_2$ derivative of formula (I)

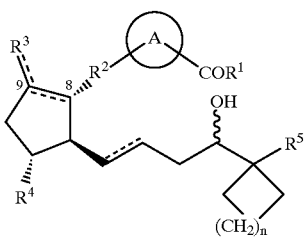

(I)

or a non-toxic salt thereof or a cyclodextrin clathrate thereof.

2. A compound according to claim 1, wherein A is a benzene ring.

3. A compound according to claim 1, wherein $R^2$ is C1–4 alkylene or C2–4 alkenylene.

4. A compound according to claim 1, wherein $R^2$ is —S—C1–4 alkylene, —S—C2–4 alkenylene.

5. A compound according to claim 1, wherein $R^2$ is C1–4 alkylene-S—.

6. A compound according to claim 3, which is
   (1) (11α,13E)-9-Oxo-11,16-dihydroxy-17,17-propano-1,6-(p-phenylene)-2,3,4,5-tetranorprost-13-enoic acid,
   (2) (11α,13E)-9-Oxo-11,16-dihydroxy-17,17-propano-1,6-(p-phenylene)-2,3,4,5-tetranorprost-13,19-dienoic acid,
   (3) (11α,13E)-9-Oxo-11,16-dihydroxy-17,17-propano-19,20-methano-1,6-(p-phenylene)-2,3,4,5-tetranorprost-13-enoic acid,
   (4) (11α,13E)-9-Oxo-11,16-dihydroxy-17,17-propano-19-methyl-1,6-(p-phenylene)-2,3,4,5-tetranorprost-13-enoic acid,
   (5) (11α,13E)-9-Oxo-11,16-dihydroxy-17,17-propano—1,6-(p-phenylene)-2,3,4,5,20-pentanorprost-13-enoic acid,
   (6) (9β,11α,13E)-9-Chloro-11,16-dihydroxy-17,17-propano-19,20-methano—1,6-(p-phenylene)-2,3,4,5-tetranorprost-13-enoic acid,
   (7) (9β, 11α,13E)-9-Chloro-11,16-dihydroxy-17,17-propano-19-methyl-1,6-(p-phenylene)-2,3,4,5-tetranorprost-13-enoic acid,
   (8) (9β,11α,13E)-9-Chloro-11,16-dihydroxy-17,17propano-1,6-(p-phenylene)-2,3,4,5,20-pentanorprost-13-enoic acid or
   (9) (9β,11α,13E)-9-Chloro-11,16-dihydroxy-17,17-propano-1,6-(p-phenylene)-2,3,4,5-tetranorprost-13,19-dienoic acid or a methyl ester thereof.

7. A compound according to claim 4, which is
   (1) (11α,8Z, 13E)-9-Acetyloxy-11,16-dihydroxy-17,17-propano-7-thia-1,6-(p-phenylene)-2,3,4,5,20-pentanorprost-8,13-dienoic acid methyl ester,
   (2) (11α,8Z, 13E)-9-Acetyloxy-11,16-dihydroxy-17,17-propano-7-thia-1,6-(p-phenylene)-2,3,4,5-tetranorprost-8,13-dienoic acid methyl ester,
   (3) (11α,8Z, 13E)-9-Acetyloxy-11,16-dihydroxy-17,17-propano-7-thia-1,6-(p-phenylene)-2,3,4,5-tetranorprost-8,13,19-trienoic acid methyl ester,
   (4) (11α,8Z, 13E)-9-Acetyloxy-11,16-dihydroxy-19-methyl-17,17-propano-7-thia-1,6-(p-phenylene)-2,3,4,5-tetranorprost-8,13-dienoic acid methyl ester or
   (5) (11α,8Z, 13E)-9-Acetyloxy-11,16-dihydroxy-17,17-propano-19,20-methano-7-thia-1,6-(p-phenylene)-2,3,4,5-tetranorprost-8,13-dienoic acid methyl ester.

8. A compound according to claim 4, which is
   (1) (11α,13E)-9-Oxo-11,16-dihydroxy-17,17-propano-7-thia-1,6-(p-phenylene)-2,3,4,5,20-pentanorprost-13-enoic acid,
   (2) (11α,13E)-9-Oxo-11,16-dihydroxy-17,17-propano-7-thia-1,6-(p-phenylene)-2,3,4,5-tetranorprost-13-enoic acid,
   (3) (11α,13E)-9-Oxo-11,16-dihydroxy-17,17-propano-7-thia-1,6-(p-phenylene)-2,3,4,5-tetranorprost-13,19-dienoic acid,
   (4) (11α,13E)-9-Oxo-11,16-dihydroxy-19-methyl-17,17-propano-7-thia-1,6-(p-phenylene)-2,3,4,5-tetranorprost-13-enoic acid or
   (5) (11α,13E)-9-Oxo-11,16-dihydroxy-17,17-propano-19,20-methano-7-thia-1,6-(p-phenylene)-2,3,4,5-tetranorprost-13-enoic acid
   or a methyl ester thereof.

9. A compound according to claim 5, which is
   (1) (11α,13E)-9-Oxo-11,16-dihydroxy-17,17-propano-6-thia-1,6-(p-phenylene)-2,3,4,5-tetranorprost-13-enoic acid or a methyl ester thereof.

10. A compound according to claim 2, wherein $R^2$ is C1–4 alkylene or C2–4 alkenylene.

11. A compound according to claim 2, wherein $R^2$ is C1–4 alkylene-S—.

12. A process for the preparation of a compound of formula (IA)

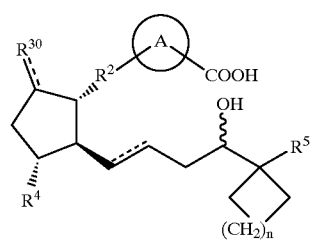

(IA)

(wherein $R^{30}$ is oxo, methylene or halogen atom and the other symbols are as defined in claim 1)
characterized by subjecting a compound of formula (IB)

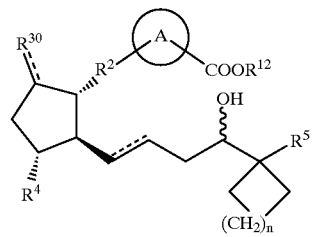

(IB)

(wherein $R^{12}$ is C1–6 alkyl and the other symbols are as defined above)
to hydrolysis using an enzyme or hydrolysis under alkaline conditions.

13. A process for the preparation of a compound of formula (IC)

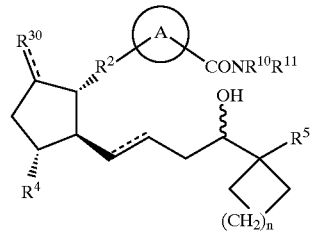

(IC)

(wherein $R^{30}$ is oxo, methylene or halogen atom, and the other symbols are as defined in claim 1)
characterized by subjecting to amidation of a compound of formula (IA)

(IA)

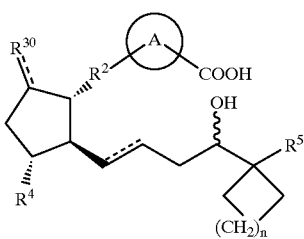

(wherein all symbols are as defined above)

and a compound of formula (II)

HNR$^{10}$R$^{11}$ (II)

(wherein all symbols are as defined above).

14. A process for the preparation of a compound of formula (IB-1)

(IB-1)

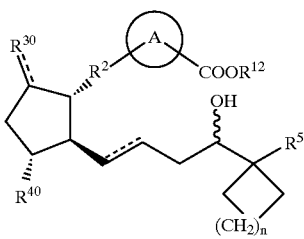

(wherein R$^{40}$ is hydrogen or hydroxy, R$^{12}$ is C1–6 and R$^{30}$ is oxo, methylene or halogen atom, and the other symbols are as defined in claim 1) characterized by subjecting to deprotection under acidic conditions a compound of formula (III)

(III)

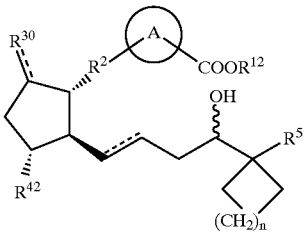

(wherein R$^{41}$ is hydrogen atom hydroxy protected by a group which can be removable under acidic conditions, R$^{60}$ is a protective group for hydroxy which may be removable under acidic conditions, and the other symbols are as defined above).

15. A process for the preparation of formula (IB-2)

(IB-2)

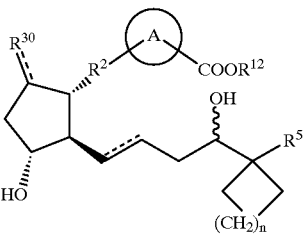

(wherein R$^{12}$ is C1–6 and R$^{30}$ is oxo, methylene or halogen atom, R$^{42}$ is C1–4 alkoxy, and the other symbls are as defined in claim 1)

characterized by subjecting to O-alkylation a compound of formula (IB-3)

(IB-3)

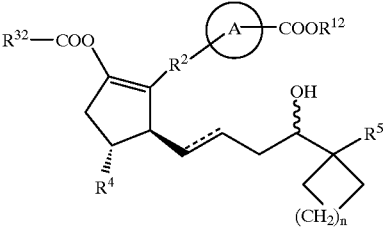

(wherein all symbols are as defined above).

16. A process for the preparation of a compound of formula (ID)

(ID)

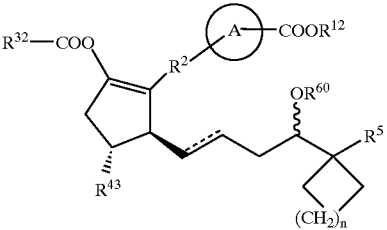

(wherein R$^{12}$ is C1–6 alkyl, R$^{32}$ is as defined in claim 1, and the other symbols are as defined in claim 1) characterized by subjecting to deprotection under acidic conditions a compound of formula (IV)

(IV)

(wherein, R$^{43}$ is hydrogen atom, hydroxy protected by a group which may be removable under acidic conditions or C1–4 alkoxy, R$^{60}$ is a protective Group for hydroxy which may be removable under acidic conditions, and the other symbols are as defined above).

* * * * *

UNITED STATES PATENT AND TRADEMARK OFFICE
CERTIFICATE OF CORRECTION

PATENT NO. : 6,262,293 B1
DATED : July 17, 2001
INVENTOR(S) : Kousuke Tani et al.

It is certified that error appears in the above-identified patent and that said Letters Patent is hereby corrected as shown below:

<u>Title page, Column 1, line 1 and Item [54],</u>
The title of Invention should read as follows:
-- ω-CYCLOALKYL-PROSTAGLANDIN $E_2$ DERIVATIVES --

Signed and Sealed this

Twenty-sixth Day of February, 2002

Attest:

JAMES E. ROGAN
*Attesting Officer*  *Director of the United States Patent and Trademark Office*